(12) United States Patent
Quadri et al.

(10) Patent No.: US 11,819,404 B2
(45) Date of Patent: *Nov. 21, 2023

(54) HEART VALVE

(71) Applicant: Edwards Lifesciences CardiAQ LLC, Irvine, CA (US)

(72) Inventors: Arshad Quadri, West Hartford, CT (US); J. Brent Ratz, Winchester, MA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/102,595

(22) Filed: Jan. 27, 2023

(65) Prior Publication Data

US 2023/0172711 A1  Jun. 8, 2023

Related U.S. Application Data

(63) Continuation of application No. 16/867,206, filed on May 5, 2020, now Pat. No. 11,589,983, which is a
(Continued)

(51) Int. Cl.
*A61F 2/24* (2006.01)
*A61F 2/848* (2013.01)

(52) U.S. Cl.
CPC .......... *A61F 2/2418* (2013.01); *A61F 2/2403* (2013.01); *A61F 2/2409* (2013.01);
(Continued)

(58) Field of Classification Search
CPC .... A61F 2/2418; A61F 2/2409; A61F 2/2412; A61F 2210/0076; A61F 2220/0016;
(Continued)

(56) References Cited

U.S. PATENT DOCUMENTS 3,657,744 A   4/1972 Ersek
3,671,979 A   6/1972 Moulopoulos
(Continued)

FOREIGN PATENT DOCUMENTS

CA   2304325 A1   10/2000
CA   2827556 A1   7/2012
(Continued)

OTHER PUBLICATIONS

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
(Continued)

*Primary Examiner* — Suzette J Gherbi
(74) *Attorney, Agent, or Firm* — Klarquist Sparkman, LLP

(57) ABSTRACT

A prosthetic heart valve includes a radially expandable annular frame and a valve body disposed inside the frame. The valve body includes three leaflets configured to regulate the flow of blood through the frame in one direction. The prosthetic heart valve also includes an annular inner skirt secured to an inner surface of the frame. The inner skirt has an inflow edge oriented toward an inflow end of the frame, an outflow edge oriented toward an outflow end of the frame, and first and second lateral edges extending from the inflow edge to the outflow edge, wherein the first lateral edge and the second lateral edge are secured together. The first lateral edge and the second lateral edge are oriented at an oblique angle relative to a plane that is perpendicular to a central longitudinal axis of the frame.

20 Claims, 21 Drawing Sheets

Related U.S. Application Data continuation of application No. 15/979,271, filed on May 14, 2018, now Pat. No. 10,646,334, which is a continuation of application No. 15/219,122, filed on Jul. 25, 2016, now Pat. No. 10,149,756, which is a continuation of application No. 13/747,327, filed on Jan. 22, 2013, now Pat. No. 9,456,896, which is a continuation of application No. 12/569,856, filed on Sep. 29, 2009, now Pat. No. 8,403,983.

(60) Provisional application No. 61/136,716, filed on Sep. 29, 2008.

(52) U.S. Cl.
CPC .......... *A61F 2/2412* (2013.01); *A61F 2/2415* (2013.01); *A61F 2/848* (2013.01); *A61F 2002/8483* (2013.01); *A61F 2002/8486* (2013.01); *A61F 2210/0076* (2013.01); *A61F 2220/005* (2013.01); *A61F 2220/0016* (2013.01); *A61F 2220/0075* (2013.01); *A61F 2230/0013* (2013.01); *A61F 2230/0054* (2013.01); *Y10T 29/49426* (2015.01)

(58) Field of Classification Search
CPC ........ A61F 2220/005; A61F 2220/0075; A61F 2230/0013; A61F 2230/0054
See application file for complete search history.

(56) References Cited

U.S. PATENT DOCUMENTS

| | | | |
|---|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,425,908 A | 1/1984 | Simon |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 5,855,601 A | 1/1999 | Bessler et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,312,465 B1 | 11/2001 | Griffin et al. |
| 6,358,277 B1 | 3/2002 | Duran |
| 6,440,164 B1 | 8/2002 | Di Matteo et al. |
| 6,458,153 B1 | 10/2002 | Bailey et al. |
| 6,482,228 B1 | 11/2002 | Norred |
| 6,527,800 B1 | 3/2003 | McGuckin, Jr. et al. |
| 6,582,462 B1 | 6/2003 | Andersen et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,947,464 B2 | 9/2005 | Schmid |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,934 B2 | 5/2012 | Styrc et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |

(56) References Cited

U.S. PATENT DOCUMENTS

| | | | |
|---|---|---|---|
| 8,403,983 B2 * | 3/2013 | Quadri | A61F 2/2412 623/2.14 |
| 8,414,644 B2 | 4/2013 | Quadri et al. | |
| 8,414,645 B2 | 4/2013 | Dwork et al. | |
| 8,444,689 B2 | 5/2013 | Zhang | |
| 8,449,599 B2 | 5/2013 | Chau et al. | |
| 8,454,685 B2 | 6/2013 | Hariton et al. | |
| 8,460,368 B2 | 6/2013 | Taylor et al. | |
| 8,470,023 B2 | 6/2013 | Eidenschink et al. | |
| 8,475,521 B2 | 7/2013 | Suri et al. | |
| 8,475,523 B2 | 7/2013 | Duffy | |
| 8,479,380 B2 | 7/2013 | Malewicz et al. | |
| 8,486,137 B2 | 7/2013 | Suri et al. | |
| 8,491,650 B2 | 7/2013 | Wiemeyer et al. | |
| 8,500,733 B2 | 8/2013 | Watson | |
| 8,500,798 B2 | 8/2013 | Rowe et al. | |
| 8,511,244 B2 | 8/2013 | Holecek et al. | |
| 8,512,401 B2 | 8/2013 | Murray et al. | |
| 8,518,096 B2 | 8/2013 | Nelson | |
| 8,518,106 B2 | 8/2013 | Duffy et al. | |
| 8,562,663 B2 | 10/2013 | Mearns et al. | |
| 8,579,963 B2 | 11/2013 | Tabor | |
| 8,579,964 B2 | 11/2013 | Lane et al. | |
| 8,579,965 B2 | 11/2013 | Bonhoeffer et al. | |
| 8,585,755 B2 | 11/2013 | Chau et al. | |
| 8,585,756 B2 | 11/2013 | Bonhoeffer et al. | |
| 8,591,570 B2 | 11/2013 | Revuelta et al. | |
| 8,597,348 B2 | 12/2013 | Rowe et al. | |
| 8,617,236 B2 | 12/2013 | Paul et al. | |
| 8,640,521 B2 | 2/2014 | Righini et al. | |
| 8,647,381 B2 | 2/2014 | Essinger et al. | |
| 8,652,145 B2 | 2/2014 | Maimon et al. | |
| 8,652,201 B2 | 2/2014 | Oberti et al. | |
| 8,652,202 B2 | 2/2014 | Alon et al. | |
| 8,652,203 B2 | 2/2014 | Quadri et al. | |
| 8,668,733 B2 | 3/2014 | Haug et al. | |
| 8,673,000 B2 | 3/2014 | Tabor et al. | |
| 8,679,174 B2 | 3/2014 | Ottma et al. | |
| 8,679,404 B2 | 3/2014 | Liburd et al. | |
| 8,685,086 B2 | 4/2014 | Navia et al. | |
| 8,721,708 B2 | 5/2014 | Seguin et al. | |
| 8,721,714 B2 | 5/2014 | Kelley | |
| 8,728,154 B2 | 5/2014 | Alkhatib | |
| 8,728,155 B2 | 5/2014 | Montorfano et al. | |
| 8,740,974 B2 | 6/2014 | Lambrecht et al. | |
| 8,740,976 B2 | 6/2014 | Tran et al. | |
| 8,747,458 B2 | 6/2014 | Tuval et al. | |
| 8,747,459 B2 | 6/2014 | Nguyen et al. | |
| 8,747,460 B2 | 6/2014 | Tuval et al. | |
| 8,758,432 B2 | 6/2014 | Solem | |
| 8,764,818 B2 | 7/2014 | Gregg | |
| 8,771,344 B2 | 7/2014 | Tran et al. | |
| 8,771,345 B2 | 7/2014 | Tuval et al. | |
| 8,771,346 B2 | 7/2014 | Tuval et al. | |
| 8,778,020 B2 | 7/2014 | Gregg et al. | |
| 8,784,337 B2 | 7/2014 | Voeller et al. | |
| 8,784,478 B2 | 7/2014 | Tuval et al. | |
| 8,784,481 B2 | 7/2014 | Alkhatib et al. | |
| 8,790,387 B2 | 7/2014 | Nguyen et al. | |
| 8,795,356 B2 | 8/2014 | Quadri et al. | |
| 8,795,357 B2 | 8/2014 | Yohanan et al. | |
| 8,808,356 B2 | 8/2014 | Braido et al. | |
| 8,828,078 B2 | 9/2014 | Salahieh et al. | |
| 8,828,079 B2 | 9/2014 | Thielen et al. | |
| 8,834,564 B2 | 9/2014 | Tuval et al. | |
| 8,845,718 B2 | 9/2014 | Tuval et al. | |
| 8,858,620 B2 | 10/2014 | Salahieh et al. | |
| 8,870,948 B1 | 10/2014 | Erzberger et al. | |
| 8,870,950 B2 | 10/2014 | Hacohen | |
| 8,876,893 B2 | 11/2014 | Dwork et al. | |
| 8,876,894 B2 | 11/2014 | Tuval et al. | |
| 8,876,895 B2 | 11/2014 | Tuval et al. | |
| 8,911,455 B2 | 12/2014 | Quadri et al. | |
| 8,926,693 B2 | 1/2015 | Duffy et al. | |
| 8,926,694 B2 | 1/2015 | Costello | |
| 8,939,960 B2 | 1/2015 | Rosenman et al. | |
| 8,945,209 B2 | 2/2015 | Bonyuet et al. | |
| 8,951,299 B2 | 2/2015 | Paul et al. | |
| 8,961,593 B2 | 2/2015 | Bonhoeffer et al. | |
| 8,961,595 B2 | 2/2015 | Alkhatib | |
| 8,974,524 B2 | 3/2015 | Yeung et al. | |
| 8,979,922 B2 | 3/2015 | Jayasinghe et al. | |
| 8,986,372 B2 | 3/2015 | Murry, III et al. | |
| 8,986,375 B2 | 3/2015 | Garde et al. | |
| 8,992,608 B2 | 3/2015 | Haug et al. | |
| 8,998,979 B2 | 4/2015 | Seguin et al. | |
| 8,998,980 B2 | 4/2015 | Shipley et al. | |
| 9,005,273 B2 | 4/2015 | Salahieh et al. | |
| 9,011,521 B2 | 4/2015 | Haug et al. | |
| 9,011,523 B2 | 4/2015 | Seguin | |
| 9,011,524 B2 | 4/2015 | Eberhardt | |
| 9,028,545 B2 | 5/2015 | Taylor | |
| 9,034,032 B2 | 5/2015 | McLean et al. | |
| 9,034,033 B2 | 5/2015 | McLean et al. | |
| 9,039,757 B2 | 5/2015 | McLean et al. | |
| 9,055,937 B2 | 6/2015 | Rowe et al. | |
| 9,066,801 B2 | 6/2015 | Kovalsky et al. | |
| 9,078,749 B2 | 7/2015 | Lutter et al. | |
| 9,078,751 B2 | 7/2015 | Naor | |
| 9,084,676 B2 | 7/2015 | Chau et al. | |
| 9,125,738 B2 | 9/2015 | Figulla et al. | |
| 9,138,312 B2 | 9/2015 | Tuval et al. | |
| 9,161,834 B2 | 10/2015 | Taylor et al. | |
| 9,173,737 B2 | 11/2015 | Hill et al. | |
| 9,180,004 B2 | 11/2015 | Alkhatib | |
| 9,186,249 B2 | 11/2015 | Rolando et al. | |
| 9,220,594 B2 | 12/2015 | Braido et al. | |
| 9,241,790 B2 | 1/2016 | Lane et al. | |
| 9,248,014 B2 | 2/2016 | Lane et al. | |
| 9,277,990 B2 | 3/2016 | Klima et al. | |
| 9,277,993 B2 | 3/2016 | Gamarra et al. | |
| 9,289,291 B2 | 3/2016 | Gorman, III et al. | |
| 9,289,296 B2 | 3/2016 | Braido et al. | |
| 9,295,551 B2 | 3/2016 | Straubinger et al. | |
| 9,326,815 B2 | 5/2016 | Watson | |
| 9,331,328 B2 | 5/2016 | Eberhardt et al. | |
| 9,339,382 B2 | 5/2016 | Tabor et al. | |
| 9,351,831 B2 | 5/2016 | Braido et al. | |
| 9,351,832 B2 | 5/2016 | Braido et al. | |
| 9,364,321 B2 | 6/2016 | Alkhatib et al. | |
| 9,445,897 B2 | 9/2016 | Bishop et al. | |
| 9,456,877 B2 | 10/2016 | Weitzner et al. | |
| 9,681,968 B2 | 6/2017 | Goetz et al. | |
| 9,700,329 B2 | 7/2017 | Metzger et al. | |
| 9,700,411 B2 | 7/2017 | Klima et al. | |
| 9,763,780 B2 | 9/2017 | Morriss et al. | |
| 9,795,479 B2 | 10/2017 | Lim et al. | |
| 9,833,313 B2 | 12/2017 | Board et al. | |
| 9,861,473 B2 | 1/2018 | Lafontaine | |
| 9,861,476 B2 | 1/2018 | Salahieh et al. | |
| 9,861,477 B2 | 1/2018 | Backus et al. | |
| 9,867,698 B2 | 1/2018 | Kovalsky et al. | |
| 9,877,830 B2 | 1/2018 | Lim et al. | |
| 9,889,029 B2 | 2/2018 | Li et al. | |
| 9,895,225 B2 | 2/2018 | Rolando et al. | |
| 9,925,045 B2 | 3/2018 | Creaven et al. | |
| 10,058,424 B2 | 8/2018 | Cooper et al. | |
| 10,226,335 B2 | 3/2019 | Cartledge et al. | |
| 10,646,334 B2 * | 5/2020 | Quadri | A61F 2/2412 |
| 11,589,983 B2 * | 2/2023 | Quadri | A61F 2/2409 |
| 2001/0007956 A1 | 7/2001 | Letac et al. | |
| 2001/0021872 A1 | 9/2001 | Bailey et al. | |
| 2001/0047200 A1 | 11/2001 | White et al. | |
| 2002/0016623 A1 | 2/2002 | Kula et al. | |
| 2002/0032481 A1 | 3/2002 | Gabbay | |
| 2002/0045929 A1 | 4/2002 | Diaz | |
| 2002/0052644 A1 | 5/2002 | Shaolian et al. | |
| 2003/0105517 A1 | 6/2003 | White et al. | |
| 2003/0120333 A1 | 6/2003 | Ouriel et al. | |
| 2003/0130729 A1 | 7/2003 | Paniagua et al. | |
| 2003/0176914 A1 | 9/2003 | Rabkin et al. | |
| 2003/0199971 A1 | 10/2003 | Tower et al. | |
| 2003/0220683 A1 | 11/2003 | Minasian et al. | |
| 2004/0093060 A1 | 5/2004 | Seguin et al. | |

(56) References Cited

U.S. PATENT DOCUMENTS

| | | |
|---|---|---|
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0070934 A1 | 3/2005 | Tanaka et al. |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0025857 A1* | 2/2006 | Bergheim ............. A61L 27/50 623/2.18 |
| 2006/0047337 A1 | 3/2006 | Brenneman |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0100687 A1 | 5/2006 | Fahey et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0071366 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0112309 A1 | 4/2009 | Jaramillo et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0216314 A1 | 8/2009 | Quadri |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2010/0036479 A1 | 2/2010 | Hill et al. |
| 2010/0094411 A1 | 4/2010 | Tuval et al. |
| 2010/0114305 A1 | 5/2010 | Kang et al. |
| 2010/0131039 A1 | 5/2010 | Chau et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256548 A1 | 10/2010 | McNamara et al. |
| 2010/0256723 A1 | 10/2010 | Murray |
| 2010/0262231 A1 | 10/2010 | Tuval et al. |
| 2010/0305685 A1 | 12/2010 | Millwee et al. |
| 2011/0004296 A1 | 1/2011 | Lutter et al. |
| 2011/0004299 A1 | 1/2011 | Essinger et al. |
| 2011/0029067 A1 | 2/2011 | McGuckin, Jr. et al. |
| 2011/0137397 A1 | 6/2011 | Chau et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0016411 A1 | 1/2012 | Tuval |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0059458 A1 | 3/2012 | Buchbinder et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0116498 A1 | 5/2012 | Chuter et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0030520 A1 | 1/2013 | Lee et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0088565 A1 | 3/2014 | Vongphakdy et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277411 A1 | 9/2014 | Bortlein et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |

(56) References Cited

U.S. PATENT DOCUMENTS

| | | |
|---|---|---|
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| DE | 102006052564 B3 | 12/2007 |
| EP | 1171059 A1 | 1/2002 |
| EP | 1255510 A1 | 11/2002 |
| EP | 1259194 B1 | 11/2002 |
| EP | 1281375 A2 | 2/2003 |
| EP | 1369098 A1 | 12/2003 |
| EP | 1472996 A1 | 11/2004 |
| EP | 1734903 A1 | 12/2006 |
| EP | 1827558 A2 | 9/2007 |
| EP | 1239901 B1 | 10/2007 |
| EP | 2124826 A1 | 12/2009 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2319458 A1 | 5/2011 |
| EP | 2398543 A1 | 12/2011 |
| EP | 2496182 A1 | 9/2012 |
| EP | 2566416 A1 | 3/2013 |
| EP | 2745805 A1 | 6/2014 |
| EP | 2749254 A1 | 7/2014 |
| EP | 2750630 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2967858 A2 | 1/2016 |
| EP | 2926766 B1 | 2/2016 |
| EP | 2985006 A1 | 2/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 9749355 A1 | 12/1997 |
| WO | 0061034 A1 | 10/2000 |
| WO | 03092554 A1 | 11/2003 |
| WO | 2004016149 A2 | 2/2004 |
| WO | 2004030569 A1 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |

(56) References Cited

FOREIGN PATENT DOCUMENTS

| | | |
|---|---|---|
| WO | 2010040009 A1 | 4/2010 |
| WO | 2010057262 A1 | 5/2010 |
| WO | 2010121076 A2 | 10/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Bavaria, Joseph E. M.D.: "CardiAQ Valve Technologies: Transcatheter Mitral Valve Implantation," Sep. 21, 2009.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

Boudjemline, Younes, et al., "Steps Toward the Percutaneous Replacement of Atrioventricular Valves," JACC, vol. 46, No. 2, Jul. 19, 2005:360-5.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. 2006.

Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.

Fanning, Jonathon P., et al., "Transcatheter Aortic Valve Implantation (TAVI): Valve Design And Evolution," International Journal of Cardiology 168 (2013) 1822-1831, Applicant believes this may have been available as early as Oct. 3, 2013.

Spillner, J. et al., "New Sutureless 'Atrial- Mitral-Valve Prosthesis' for Minimally Invasive Mitral Valve Therapy," Textile Research Journal, 2010, in 7 pages, Applicant believes this may have been available as early as Aug. 9, 2010.

Karimi, Houshang, et al., "Percutaneous Valve Therapies," SIS 2007 Yearbook, Chapter 11, pp. 1-11.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.

Sondergaard, Lars, et al., "Transcatheter Mitral Valve Implantation: CardiAQ™," Applicant believes this may have been presented at TCT 2013.

Sondergaard, Lars, et al., "Transcatheter Mitral Valve Implantation: CardiAQ™," Applicant believes this may have been presented at EuroPCR 2013.

Sondergaard, Lars, "CardiAQ TMVR FIH—Generation 2," Applicants believe this may have been presented in 2014 at the TVT symposium.

Ratz, J. Brent, CardiAQ Valve Technologies, "Innovations in Heart Valve Therapy," In3 San Francisco, Jun. 18, 2008, PowerPoint presentation in 19 slides.

Ratz, J. Brent, "LSI EMT Spotlight," May 15, 2009.

Ratz, J. Brent, "In3 Company Overview," Jun. 24, 2009.

"Company Overview," at TVT on Jun. 25, 2009.

Ruiz, Carlos E., "Overview of Novel Transcatheter Valve Technologies," Applicant believes this may have been presented on May 27, 2010 at EuroPCR.

"Update," Applicant believes this may have been presented on Jun. 6, 2010 at TVT.

Mack, Michael, M.D., "Antegrade Transcatheter Mitral valve Implantation: A Short-term Experience in Swine Model," Applicant believes this may have been presented on May 2011 at TVT.

Mack, Michael, M.D., "Antegrade Transcatheter Mitral valve Implantation: On-Going Experience in Swine Model," Applicant believes this may have been presented on Nov. 2011 at TCT.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Quadri, Arshad M.D., "Transcatheter Mitral Valve Implantation (TMVI) (An Acute In Vivo Study)," Applicant believes this may have been presented on Sep. 22, 2010 at TCT.

Masson, Jean-Bernard, et al., "Percutaneous Treatment of Mitral Regurgitation," Circulation: Cardiovascular Interventions, 2:140-146, Applicant believes this may have been available as early as Apr. 14, 2009.

Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.

(56) References Cited

OTHER PUBLICATIONS

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.

Taramasso et al.: "New devices for TAVI: technologies and initial clinical experiences" http://www.nature.com/hrcardio/journal/v11/n3/full/nrcardio.2013.221.html?message-global=remove#access. Jan. 21, 2014.

Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).

Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.

Feldman, Ted, MD. "Prospects for Percutaneous Valve Therapies," Circulation 2007;116:2866-2877. Applicant believes that this may be available as early as Dec. 11, 2007.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.

Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

"CardiAQTM Valve Technologies reports Successful First-in-Human Trans-Apical implantation of its Second Generation Transcatheter Mitral Valve," CardiAQ Valve Technologies Press Release, May 20, 2014.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Banai MD, Shmuel, The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Neovasc corporate presentation, Oct. 2009, available at http://www.neovasc.com/investors/documents/Neovasc-Corporate-Presentation-October-2009.pdf.

NJ350: Vote for Your Favorite New Jersey Innovations, Jun. 27, 2014, http://www.kilmerhouse.com/2014/06/nj350-vote-for-your-favorite-new-jersey-innovations/.

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

Bavaria, Joseph E. M.D et al.: "Transcatheter Mitral Valve Implantation: The Future Gold Standard for MR?," Applicant requests the Examiner to consider this reference to be prior art as of Dec. 2010.

Ratz, J., Presentation. CardiAQ Valve Technologies, "Innovations in Heart Valve Therapy," In3 San Francisco, Jun. 18, 2008, PowerPoint presentation in 19 slides.

* cited by examiner

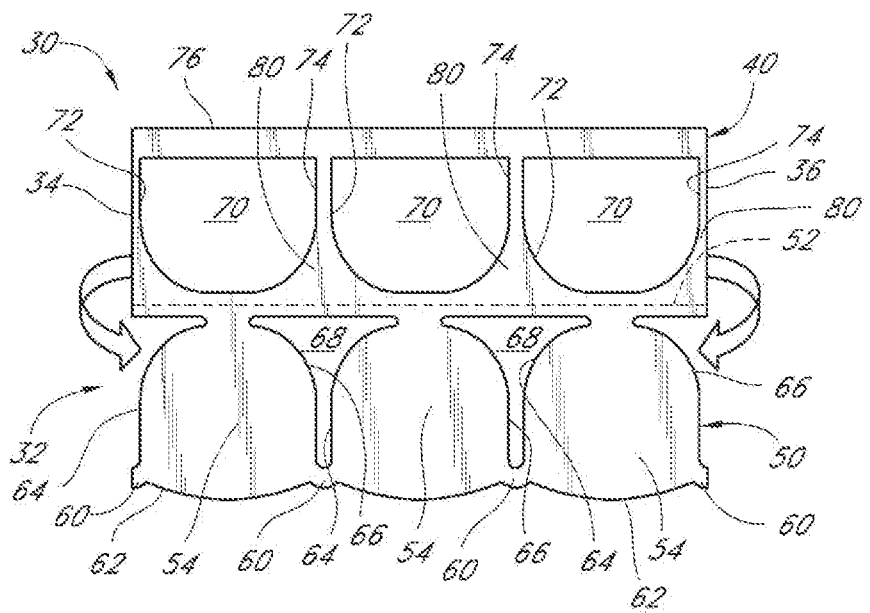
FIG. 1
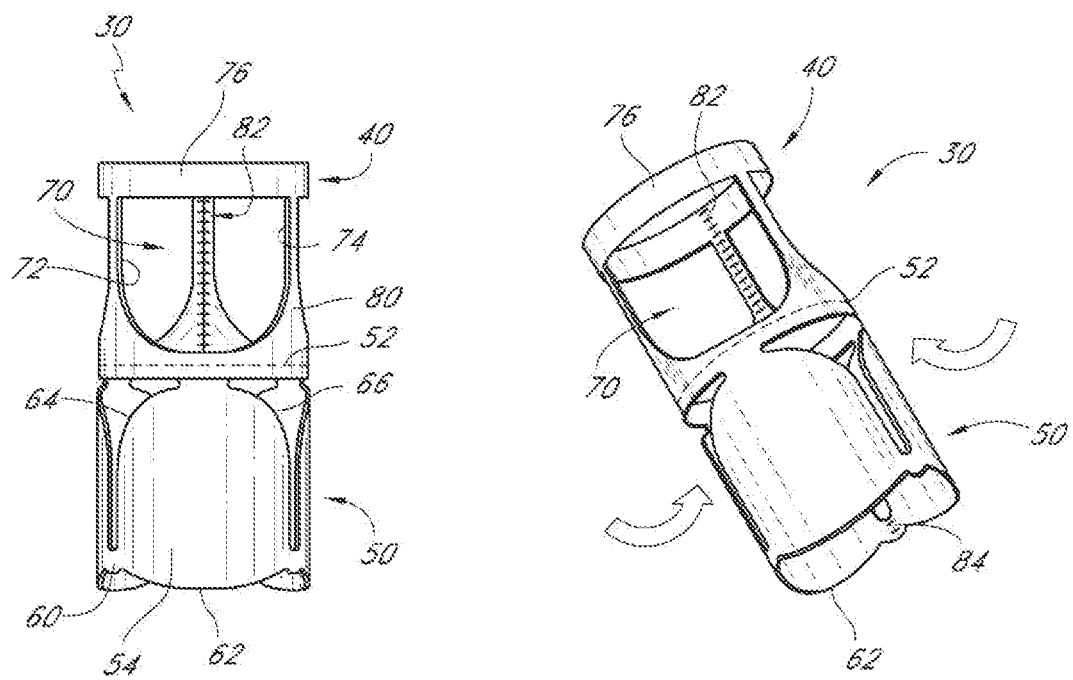
FIG. 2A
FIG. 2B

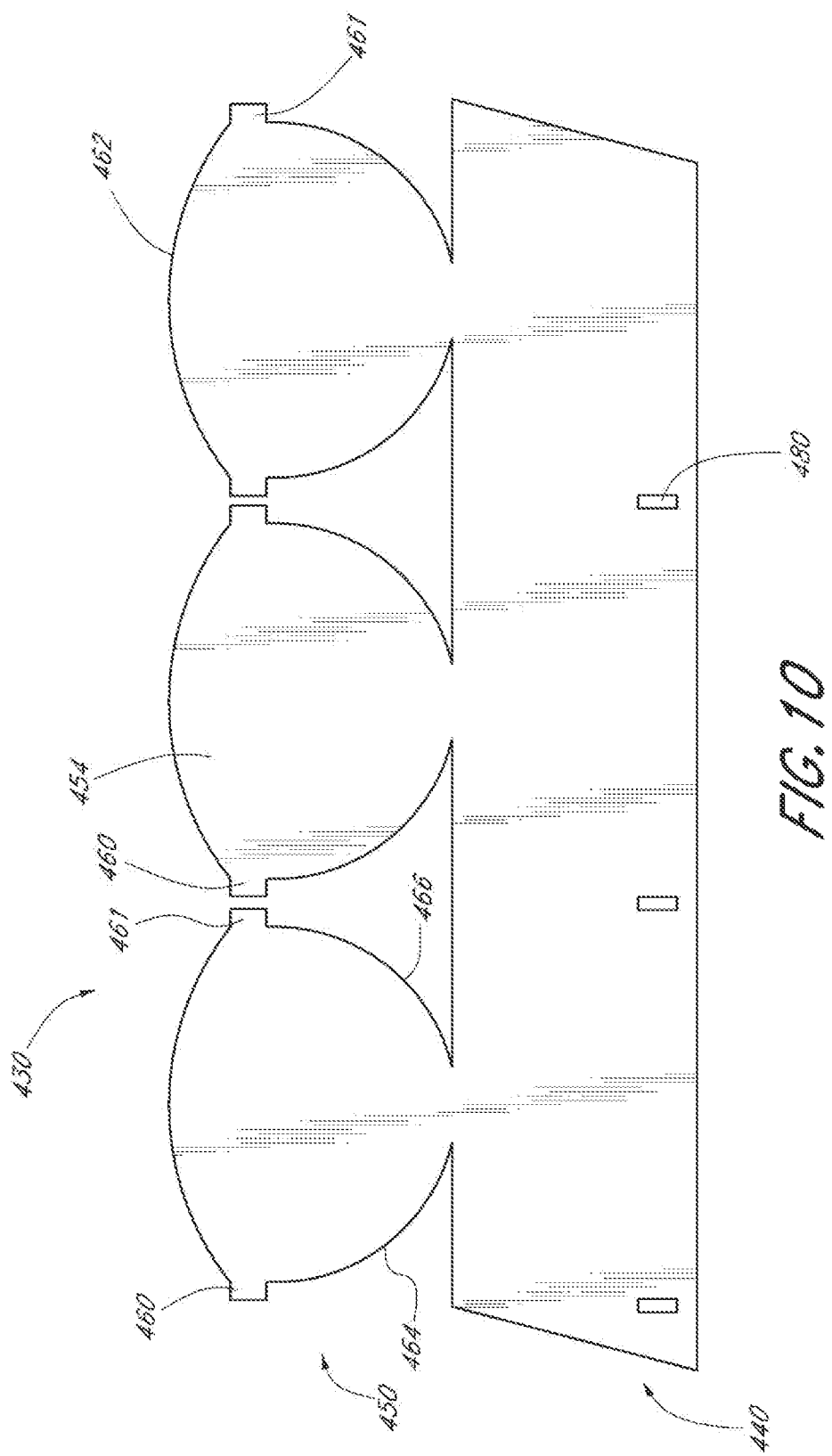

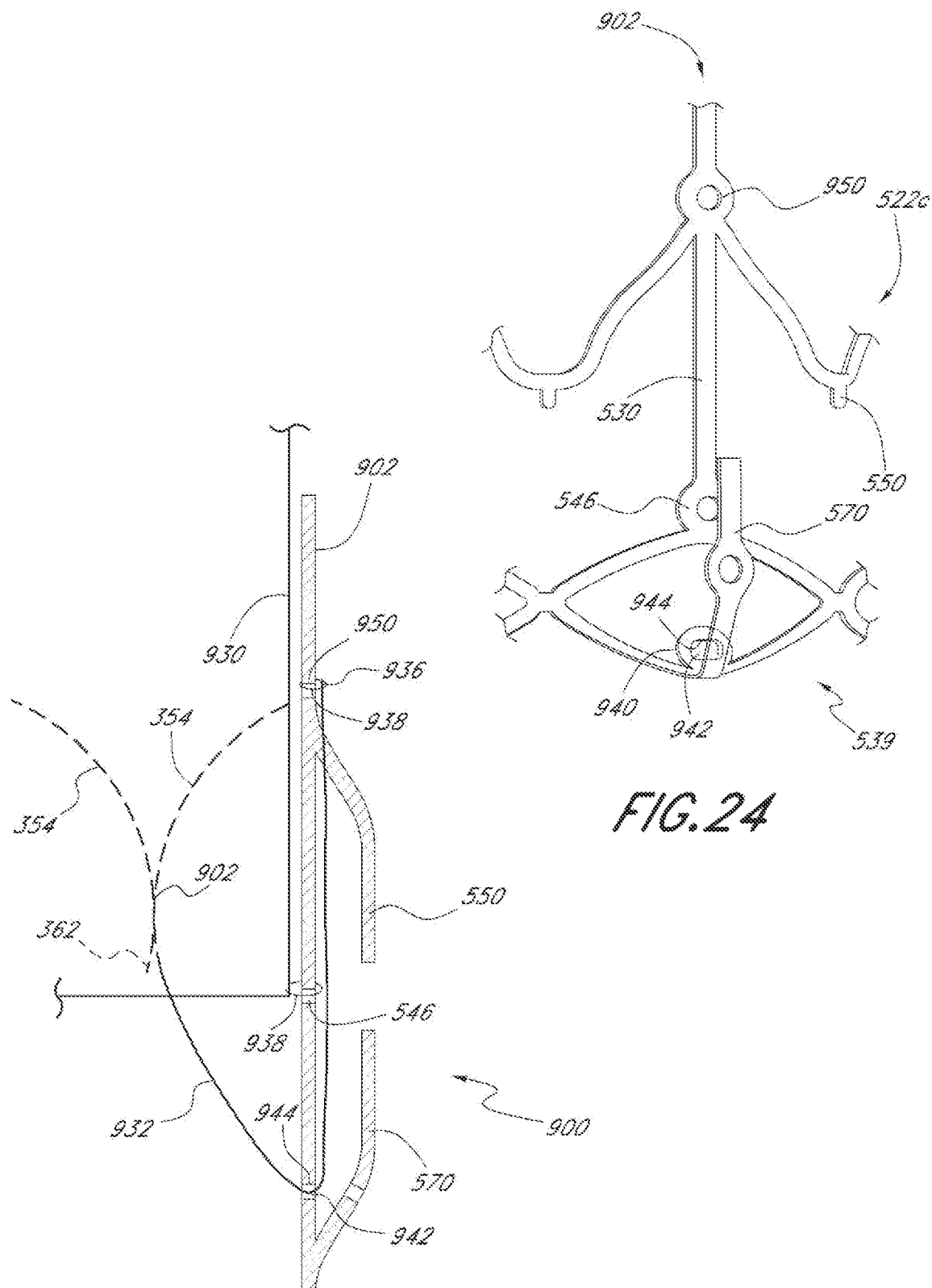

HEART VALVE

CROSS-REFERENCE TO RELATED APPLICATIONS

This application is a continuation of U.S. application Ser. No. 16/867,206, filed May 5, 2020, which is a continuation of U.S. application Ser. No. 15/979,271, filed May 14, 2018, now U.S. Pat. No. 10,646,334, which is a continuation of U.S. application Ser. No. 15/219,122, filed Jul. 25, 2016, now U.S. Pat. No. 10,149,756, which is a continuation of U.S. application Ser. No. 13/747,327, filed Jan. 22, 2013, now U.S. Pat. No. 9,456,896, which is a continuation of U.S. application Ser. No. 12/569,856, filed Sep. 29, 2009, now U.S. Pat. No. 8,403,983, which claims the benefit of U.S. Provisional Application No. 61/136,716, which was filed on Sep. 29, 2008. U.S. application Ser. Nos. 13/747,327 and 12/569,856, are each incorporated by reference herein in its entirety and are to be considered a part of this specification.

BACKGROUND

Field of the Invention

The present invention relates to replacement heart valves. More specifically, the invention relates to tissue- or simulated tissue-based replacement heart valves.

Description of the Related Art

Human heart valves, which include the aortic, pulmonary, mitral and tricuspid valves, function essentially as one-way valves operating in synchronization with the pumping heart. The valves allow blood to flow in a downstream direction, but block blood from flowing in an upstream direction. Diseased heart valves exhibit impairments such as narrowing of the valve or regurgitation. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatus to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable stent that is then delivered to the native valve's annulus.

Development of replacement heart valves that can be compacted for delivery and then controllably expanded for controlled placement has proven to be particularly challenging. Further, durability concerns, particularly with tissue-based replacement valves, are at the forefront. For example, tissue-based valves typically include components that are sewn together, and such seams can be sources of stress concentrations, particularly when relatively thin tissue is used.

SUMMARY

Accordingly, there is in the need of the art for a tissue-based heart valve with enhanced durability and which lends itself to compaction and controlled expansion in a minimally invasive and/or percutaneous delivery.

In accordance with one embodiment, the present invention provides a replacement heart valve that comprises a valve body having an outer layer and an inner layer. The outer layer is tubular and has a longitudinal axis, an upstream end and a downstream end, and is formed from a thin, flexible material. The inner layer is generally tubular, has a longitudinal axis generally collinear with the outer layer, and is positioned within the tubular outer layer. The inner layer is formed from a thin, flexible material and defines a plurality of leaflets adapted to move between an open state and a coapted state. Each leaflet has a side edge and a downstream portion. Adjacent leaflets of the inner layer are connected by a commissural portion. The leaflets are attached to the outer layer along the leaflet side edges, and the commissural portions are attached to the outer layer downstream of at least a portion of the leaflet side edges;

In one such embodiment, the inner and outer layers are constructed from a single, contiguous section of the flexible material. In another embodiment, the inner and outer layers are folded relative to one another at the upstream end so that the inner layer is contiguous with the outer layer at the upstream end.

In another embodiment, the outer layer comprises a commissural slit, and an edge of one of the commissural portions of the inner layer extends at least partially through the slit. In one such embodiment, the outer layer comprises a leaflet slit shaped to complement a corresponding leaflet side edge, and the leaflet side edge extends at least partially through the slit.

In yet another embodiment, the outer layer has a plurality of windows formed therethrough, and the windows are configured so that, when the leaflets are in the coapted state, blood readily flows through the windows.

In a further embodiment, a replacement heart valve comprises a valve body and an elongate stent that can be radially compacted to a compacted state and radially expanded to an expanded state. The stent having a longitudinal axis and the valve body is attached to the stent.

In one such embodiment, an outer layer of the valve body is on an outer side of the stent and an inner layer of the valve body is on an inner side of the stent so that the stent is sandwiched between the inner and outer layers.

In another such embodiment, the valve body is positioned so that the stent is adjacent an outer surface of the valve body. In some such embodiments, an outer layer of the valve body is connected to the stent, and an inner layer of the valve body is directly connected to the outer layer, but is not directly connected to the stent. In additional such embodiments, when the leaflets are in an open position, an outer layer of the valve body is interposed between open leaflets and the stent.

In yet another such embodiment, the stent has a foreshortening portion, which foreshortening portion is configured so that as the stent is radially compacted, the foreshortening portion longitudinally expands, and as the stent is radially expanded, the foreshortening portion longitudinally contracts.

In one embodiment with such a foreshortening stent, at least a portion of the valve body is disposed at least partially within the foreshortening portion, and the valve body is attached to the stent at one or more connecting points, which connecting points are generally aligned with an axial point along the stent longitudinal axis, so that during foreshortening the stent longitudinally moves relative to the valve body without longitudinally stretching or crushing the valve body. One such embodiment additionally comprises a longitudinally expandable material that is directly connected to the stent and to the valve body. The flexible material is directly connected to the stent at one or more connection points that are longitudinally spaced from the axial point.

In another embodiment having a foreshortening stent, the stent additionally comprises a non-foreshortening portion, and a valve body is maintained within the non-foreshortening portion.

In accordance with another embodiment, the present invention provides a method of making a replacement heart valve. The method includes providing a flat, flexible source material and cutting the flat material according to a desired pattern. The pattern defines first and second pattern ends, a skirt portion, and a leaflet portion. The leaflet portion defines a plurality of leaflets, commissures extending between adjacent leaflets, and each leaflet having side edges. The method additionally comprises adjoining the first and second pattern ends so as to form the flat material into a tube, folding the leaflet portion relative to the skirt portion along a fold line so that the leaflet portion is generally within the skirt portion, attaching the commissures to the skirt portion, and attaching the leaflet side edges to the skirt portion.

Another embodiment additionally comprises providing a form having a shape that is substantially the negative of a desired shape of the valve in a closed state, the form having leaflet shaping portions, and after the flat material has been formed into a tube and the commissures attached to the skirt portion, placing the valve upon the form so that the leaflets engage the leaflet shaping portions, and attaching the leaflet side edges to the skirt portion when the leaflets are engaged with the leaflet shaping portions.

A further such embodiment additionally comprises forming leaflet slits in the skirt portion, the leaflet slits generally corresponding the a desired curvature of the leaflets, and placing the valve upon the form so that the leaflets engage the leaflet shaping portions comprises extending the leaflet side edges through the leaflet slits in the skirt portion.

Another embodiment additionally comprises providing an elongate stent, and attaching the skirt portion to the stent.

In accordance with still another embodiment, a method of treating valve insufficiency of a patient by delivering a replacement heart valve is provided. The method comprises providing a replacement heart valve comprising a valve body attached to a stent, the valve body having an upstream end and a plurality of leaflets adapted to open and close, the leaflets each having a downstream portion, the stent being elongate and having an upstream end, a downstream end, and a longitudinal midpoint halfway between the upstream and downstream ends, the stent having an annulus attachment zone adapted to engage a native valve annulus, the annulus attachment zone disposed at or adjacent the downstream end of the stent, and positioning the heart valve within a patient's heart so that the annulus attachment zone of the stent engages a patient's mitral annulus, and the longitudinal midpoint of the stent is disposed within the patient's left atrium.

In one such embodiment, the step of positioning the heart valve comprises positioning the valve so that substantially all of the stent is disposed in the patient's mitral annulus or left atrium.

In another embodiment, the valve body is connected to the stent so that the leaflets are substantially within the left atrium. In other embodiments, the valve body is connected to the stent so that the downstream ends of the leaflets are disposed generally within the mitral annulus.

In accordance with yet another embodiment, the present invention provides a flexible tubular valve body defining a plurality of leaflets connected to a longitudinally stretchable portion. The valve body is less longitudinally stretchable than the longitudinally stretchable portion. In one such embodiment, the valve body and connected longitudinally stretchable portion are mounted on a stent that has a foreshortening portion, and a portion of the valve body overlaps the foreshortening portion so the when the stent foreshortens, the longitudinally stretchable portion preferentially stretches or contracts so that the valve body moves longitudinally relative to the stent.

In another embodiment, a valve body having an inner layer and an outer layer, the inner layer defining a plurality of leaflets, is constructed by separately forming the inner and outer layers, attaching an upstream end of the inner layer to the outer layer, and attaching side edges and commissural tabs of the leaflets to the outer layer. In one such embodiment, slits are formed through the outer layer, and one or more of the commissural tabs and leaflets are drawn at least partially through corresponding slits and then secured to the outer layer.

Other inventive embodiments and features are disclosed below.

BRIEF DESCRIPTION OF THE DRAWINGS

FIG. 1 illustrates a flat pattern for cutting a flat source material to create an embodiment of a heart valve body.

FIG. 2A is a side view of tissue cut according to the flat pattern of FIG. 1 and formed into a tube.

FIG. 2B is a perspective view of the assembly of FIG. 2A.

FIG. 10 shows a flat pattern for cutting a flat source tissue to form yet another embodiment of a heart valve body.

FIG. 24 is a partial side view of a stent for use in accordance with the assembly of FIG. 23.

FIG. 25 is a schematic partial side view of a vertical cross-section of the heart valve of FIG. 24.

DETAILED DESCRIPTION OF PREFERRED EMBODIMENTS

Figure 3A:
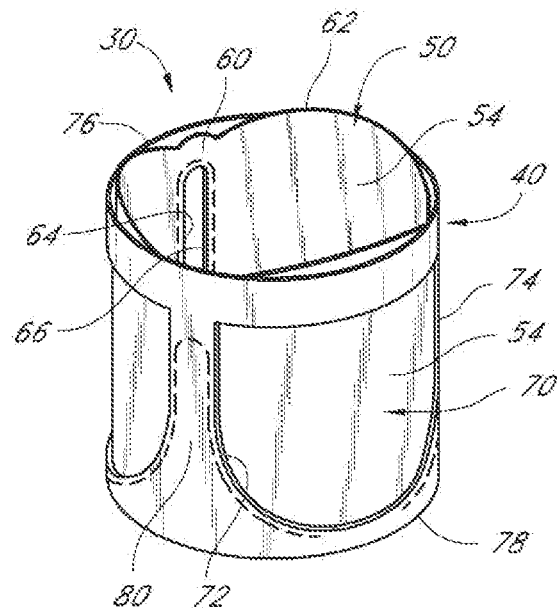
FIG. 3A is a perspective view of the assembly of FIG. 1 formed into a heart valve body and shown in an open position.

The present specification and drawings disclose aspects and features of the invention in the context of several embodiments of replacement heart valves and portions thereof that are configured for replacement of natural heart valves in a patient. These embodiments may be discussed in connection with replacing specific valves such as the patient's aortic or mitral valve. However, it is to be understood that the context of a particular valve or particular features of a valve should not be taken as limiting, and features of any one embodiment discussed herein can be combined with features of other embodiments as desired and when appropriate.

With initial reference to FIGS. 1-3, a structure for a heart valve body 30, along with methods of making the valve body 30, are described. In this embodiment, the heart valve body is constructed of a tissue-based media such as bovine pericardium. Of course, other materials such as equine and porcine pericardium, vascular tissue, as well as other natural and manmade materials that are thin, flexible and durable, may be employed. Preferably, the tissue is provided as a flat source material.

FIG. 1 illustrates a flat pattern 32 for cutting flat source tissue to form an embodiment of a heart valve body 30. More specifically, source tissue preferably is laid out in a flat format, and then cut according to the illustrated flat pattern 32. Preferably the tissue is cut by a laser, but other cutting modes and methods can be employed.

As illustrated in FIG. 1, the flat source tissue cut according to the pattern has first and second pattern ends 34, 36. A skirt portion 40 and a leaflet portion 50 are separated by a fold line 52. The illustrated leaflet portion 50 comprises three leaflets 54 connected to one another at commissural tab portions 60. Each leaflet 54 has a downstream edge 62 that preferably is curved, and also has curved, generally-opposing first and second leaflet side edges 64, 66. In accordance with the pattern 32 in the illustrated embodiment, the adjacent leaflets 54 are defined by voids 68 cut between them.

The illustrated skirt portion 40 comprises three windows 70 that are defined by apertures cut through the flat source tissue. The windows 70 each have first and second side edges 72, 74, which first and second window side edges 72, 74 are generally complementary in curvature to the first and second side edges 64, 66, respectively, of the corresponding leaflets 54. A downstream ring 76 of the skirt portion 40 preferably runs continuously from the first pattern end 34 to the second pattern end 36. Similarly, an upstream ring portion 78 of the flat pattern 32 runs continuously from the first pattern end 34 to the second pattern end 36 at and adjacent the fold line 52. Leaflet supports 80 are defined between adjacent windows 70, and share the first and second window side edges 72, 74. The leaflet supports 80 extend from the upstream ring 78 to the downstream ring 76. In the illustrated embodiment, the first and second pattern ends 34, 36 are arranged to evenly split one of the leaflet supports 80 of the skirt portion 40 and one of the commissural tab portions 60 of the leaflet portion 50.

With reference to FIGS. 2A and 2B, once the pattern 32 has been cut from the flat source tissue, the cut tissue is rolled and the first and second pattern ends 34, 36 are joined together to create a tubular structure as shown. In the illustrated embodiment, the first and second pattern ends 34, 36 are joined together by a seam that preferably employs a conventional suture material. As such, a seam 82 in the skirt portion 40 connects the first and second pattern ends 34, 36 so as to complete the leaflet support 80, and a seam 84 in the leaflet portion 50 completes the commissural tab 6.

Although sutures are used in the illustrated embodiment, it is to be understood that other methods and apparatus can be used to join the first and second ends and to make other connections when forming valve bodies. For example, in other embodiments, adhesives, clips or the like may be employed.

Figure 3B:
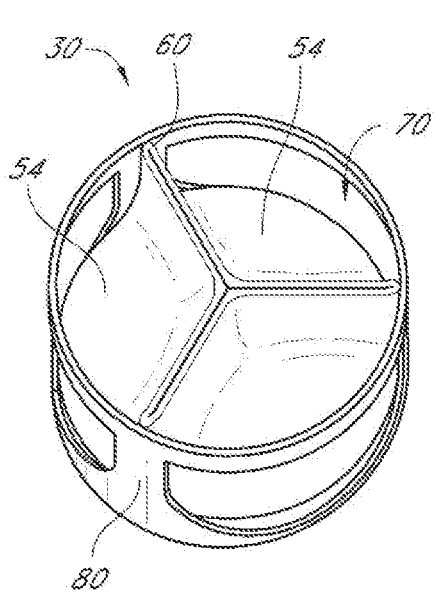
FIG. 3B shows the heart valve body of FIG. 3A in a closed condition and viewed from a downstream position.
Figure 3C:
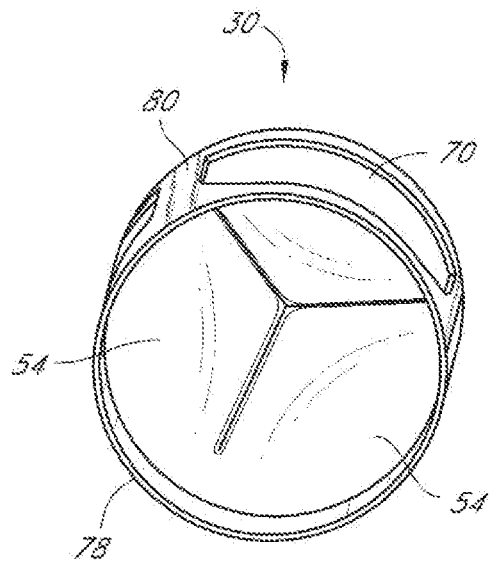
FIG. 3C shows the heart valve body of FIG. 3A in a closed condition and viewed from an upstream position.

With additional reference to FIGS. 3A-C, once the first and second pattern ends 34, 36 are joined so as to create a tubular structure, the leaflet portion 50 can then be folded about the fold line 52 and inverted into the interior of the skirt portion 40. As such, the leaflet portion 50 of the valve body 30 sits within and generally abutting the skirt portion 40.

With continued reference to FIGS. 3A-C, once folded so that the leaflet portion 50 is within the skirt portion 40, the leaflet and skirt portions 50, 40 are attached to one another. More specifically, the first and second leaflet edges 64, 66 are attached to the respective first and second window side edges 72, 74 of corresponding leaflet supports 80. As shown, the edges 64, 66, 72, 74 preferably generally align so as to be conducive to being connected by a seam. Further, the commissural tabs 60 are attached to the downstream ring 76 of the skirt portion 40. Preferably, such attachments are accomplished through stitching in a conventional manner using conventional materials such as suture material. However, other materials, such as adhesives, may also be used. Additionally, in some embodiments, the commissural tabs can be secured to the skirt by a clip in lieu of or in addition to a stitching. Also, in still further embodiments, the leaflet and skirt portions can be formed separately and then connected at, for example, an upstream ring. Such an alternative will apply to other embodiments and features discussed herein.

Once the leaflet portion 50 has been appropriately connected to the skirt portion 40, the valve body 30 can move between the open condition depicted in FIG. 3A to the closed condition depicted in FIGS. 3B and 3C. As shown in FIGS. 3B and 3C, when closed, the valve leaflets 54 coapt with one another so as to block blood from flowing upstream between the leaflets 54. Also, since the leaflets 54 are sewn securely onto the skirt 40 at the supports 80, no blood will flow between the skirt portion 40 and leaflet portion 50 at the upstream end 78 of the valve body 30, thus preventing paravalvular leaks. In the illustrated embodiment, the windows 70 of the skirt portion 40 generally align with the leaflets 54. As such, when the leaflets 54 are in the closed condition, blood flow is deflected by the leaflets 54 and readily flows through the windows 70.

The valve body 30 of FIGS. 3A-C is appropriate to use to replace a patient's native valve and embodiments employing features described in connection with the illustrated valve body 30 can be used alone or in conjunction with a stent frame. For example, in one embodiment, a valve body 30 as in FIG. 3A can be installed into the annulus of a patient's native aortic valve. In such an embodiment, the upstream ring 78 is sewn or otherwise attached to the native valve annulus, and the downstream ring 76 is attached to the aorta downstream of the annulus. As such, the valve body 30 sits in the aortic sinus. In this embodiment, the windows 70 of the skirt portion 40 are particularly useful in that when the leaflets 54 coapt, blood readily flows through the windows 70 and into the cardiac arteries that branch off of the aortic sinus.

Figures 4A, 4B:
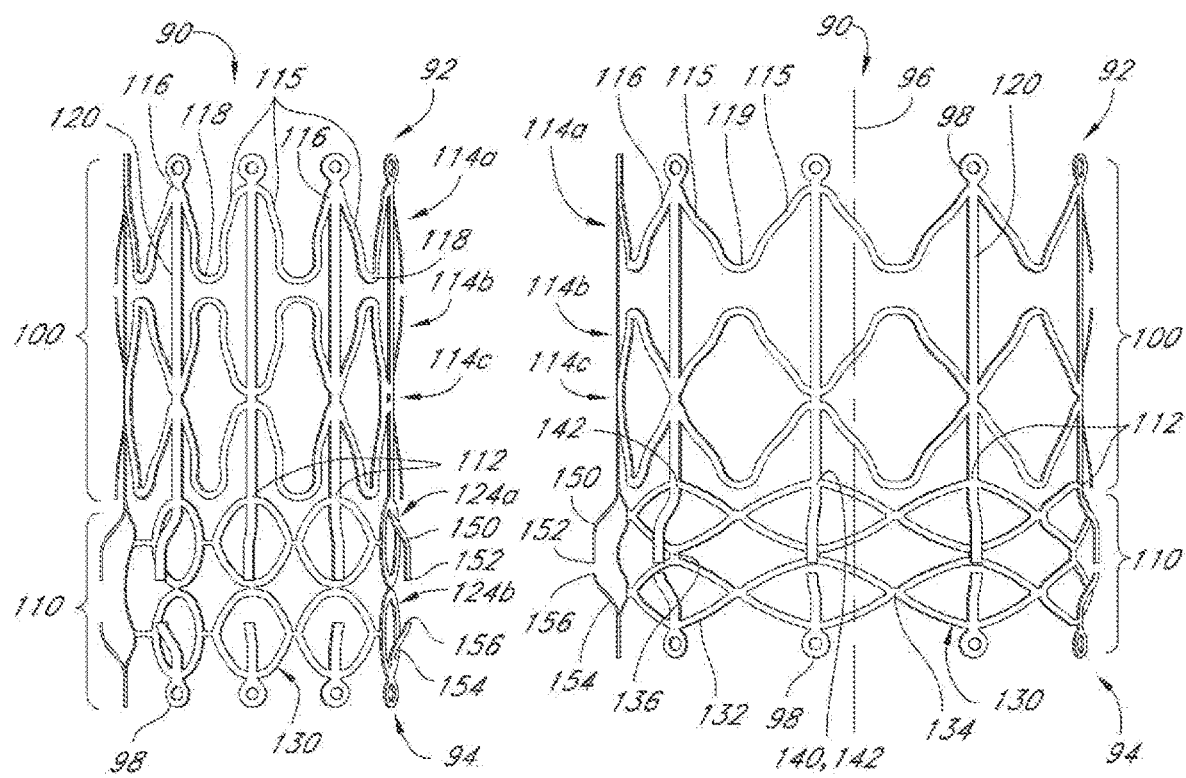
FIG. 4A is a schematic view of an embodiment of a stent frame, shown in a compacted state.
FIG. 4B shows the stent frame of FIG. 4A in an expanded state.
Figure 5:
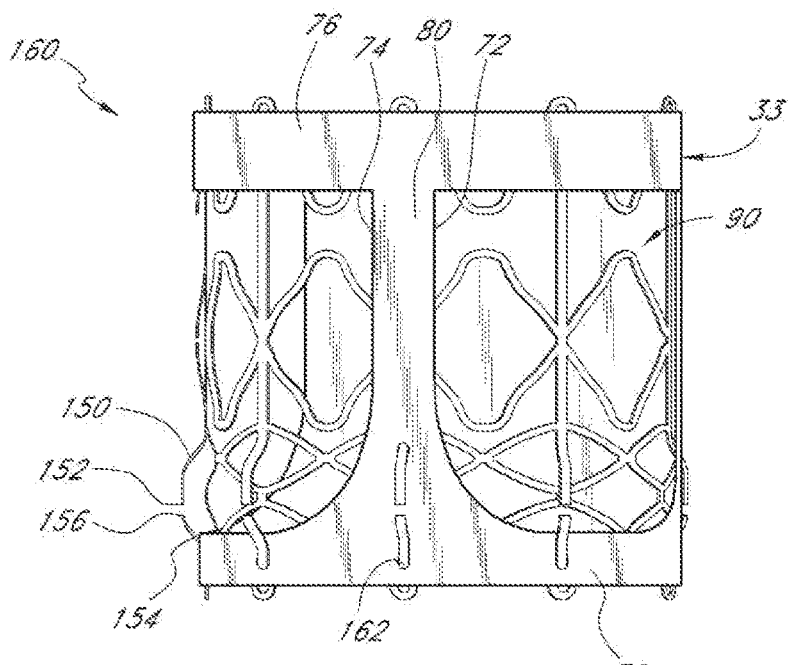
FIG. 5 is a side view of the stent frame of FIGS. 4A and B with the valve body of FIGS. 1-3 mounted thereon.

With reference next to FIGS. 4 and 5, a heart valve body 30 as in FIG. 3 can be mounted onto a stent 90. Such a stent can be of various designs and characteristics. For example, such a stent may be self-expandable, balloon-expandable, a hybrid, or the like.

With particular reference to FIGS. 4A and 4B, the illustrated stent frame 90 embodiment supports the valve body 30 and can be expanded from a compacted state as shown in FIG. 4A to an expanded state as shown in FIG. 4B. The illustrated stent 90 preferably is a self-expanding stent constructed of a flexible material, preferably a shape memory material such as nitinol. As it is self-expanding, the stent 90 is in a fully opened state, as depicted in FIG. 4B, when relaxed. The illustrated stent 90 preferably is elongate from a first end 92 to a second end 94 and is tubular with a longitudinal axis 96 and a generally circular cross section. It is to be understood that in other embodiments stents can have a non-circular cross section, such as a D-shape, an oval or an otherwise ovoid cross-sectional shape. In the illustrated embodiment a plurality of spaced apart eyelets 98 are provided both at the first end 92 and at the second end 94 of the stent frame 90. Other embodiments may be constructed without such eyelets 98.

The illustrated stent frame 90 has a non-foreshortening portion 100 and a foreshortening portion 110. The portions are joined at a transition 112 between the first and second ends 92, 94. Foreshortening refers to a behavior in which the length of the stent 90 in the foreshortening portion 110 decreases as the radius of the stent increases from the compacted state to the expanded, deployed state. As such, in FIG. 4A, which shows the stent frame 90 in a compacted state, the foreshortening portion 110 of the stent frame 90 is longer than when the stent is in the expanded state illustrated in FIG. 4B.

With continued reference to FIG. 4B, the non-foreshortening portion 100 of the illustrated stent 90 comprises a plurality of rows or rings 114a-c of circumferentially expansible elements, or struts 115, arranged in a zigzag pattern. The struts 115 are configured to expand and contract with a change in radius of the stent 90. In the illustrated embodiment, the stent has three such rings 114a-c. It is to be understood that more or fewer rings can be employed as desired to accomplish the purposes of this stent frame. In the illustrated embodiment, the respective ends of each circumferential undulating strut 115 joins an adjacent strut 115 at an apex 116, 118 which is, in at least some embodiments, an area of preferential bending. In the illustrated embodiment, the zigzag pattern of a first 114a and a third ring 114c are generally in phase with one another, while the struts 115 of a second ring 114b between the first and third rings 114a, 114b are generally out of phase with those of the first and third rings. It is to be understood that, in other embodiments, all or most of the rings can be in phase with one another or out of phase as desired.

With continued reference to FIG. 4B, longitudinal struts 120 extend transversely across the rings 114a-c of the non-foreshortening portion 100 from the first end 92 of the frame 90 to the transition 112. More particularly, each ring 114 shares a common longitudinal strut 120. The longitudinal struts 120 extend through apices 116 of adjacent rings 114, and preferably extend the entire length of the non-foreshortening portion 100. Preferably, the longitudinal struts 120 comprise a non-expandable rod or bar. The apices 116 that are connected to the longitudinal struts 120 are referred to as "connected" apices 116. Apices 118 not connected to longitudinal struts 120 are referred to as "free" apices 118.

As noted above, the longitudinal struts 120 are not substantially expandable in a longitudinal direction. As such, even though the undulating struts 115 provide flexibility in radial expansion or compaction, as the stent 90 changes radial size between the compacted and expanded states, the longitudinal length of the stent in the non-foreshortening portion 100 remains substantially unchanged. In other embodiments, the longitudinal struts may include expansible elements that may allow the struts to expand somewhat longitudinally. However, such longitudinal expansion would not be directly tied to any change in strut radius.

With continued reference to FIGS. 4A and 4B, the foreshortening portion 110 of the illustrated stent frame comprises a first and a second circumferential ring 124a, 124a that are each made up of interconnected cells 130. Each cell 130 comprises a plurality of strut members 132 that are interconnected in such a way that when the stent expands radially, the cell 130 becomes longitudinally shorter. In the illustrated embodiment, each cell 130 is enclosed and is configured in generally a diamond-shaped pattern. Circumferential and longitudinal cell connectors 134, 136 connect adjacent cells 130 to one another. An upper end 140 of each cell 130 in the first ring 124a is connected to a second end 142 of a corresponding longitudinal strut 120 of the non-foreshortening portion 100 at the transition 112.

Although the illustrated foreshortening cells 130 are arranged in a diamond pattern, it is to be understood that other configurations can be employed. For example, in other embodiments, the foreshortening cells can be generally oval-shaped, and in further embodiments the cells may not be fully enclosed. As discussed above and illustrated in FIGS. 4A and 4B, when the illustrated stent 90 is expanded from the compacted state to the expanded state, the non-foreshortening portion 100 of the stent remains substantially the same length while the foreshortening portion 110 of the stent becomes substantially shorter in length.

With continued reference to FIGS. 4A and 4B, a plurality of first anchors 150 extend from the transition 112 into the foreshortening portion 110. Preferably, each of the anchors 150 also extends generally radially outwardly from the stent 90 so that a tip 152 of each first anchor 150 is spaced from the cells 130. Similarly, a plurality of second anchors 154 extend from the foreshortening cells 130 at or adjacent the second end 94 of the stent frame 90 and extend into the foreshortening portion and radially outwardly from the stent so that a tip 156 of each second anchor 154 is spaced from the cells 130. A first distance is defined between the tips 152, 156 of opposing first and second anchors 150, 154 when the stent 90 is in the compacted state, and a second distance is defined between the tips 152, 156 of opposing first and second anchors 150, 154 when the stent 90 is in the expanded state. As shown, the second distance is substantially less than the first distance. This arrangement enables the foreshortening portion 110, with its anchors 150, 154, to grasp onto tissues so as to hold the stent in place.

In preferred embodiments, the stent 90 may be deployed into a heart valve annulus, and positioned when compacted so that the tips 152, 156 of the opposing first and second anchors 150, 154 are disposed on opposite sides of the native annulus. As the stent is expanded, the opposing first and second anchors are drawn closer together so as to grasp opposite sides of the native annulus and securely hold the stent in position. As such, the stent can be held securely in position without requiring a substantial radial force against the native annulus. Applicant's U.S. patent application Ser. No. 12/084,586, which was published on Aug. 27, 2009 as U.S. Publication No. 2009/0216314, discusses embodiments of foreshortening stents with anchors, and can be referred to for further discussion of certain aspects of the illustrated stent embodiment. The discussion in the above application concerning structure and operation of embodiments of a foreshortening stent, particularly a foreshortening stent having anchors, is expressly incorporated by reference herein.

In the illustrated embodiment, the stent is made of a shape-memory alloy, specifically nitinol. It is to be understood, however, that other materials, including metals, metal alloys and non-metals can be employed as appropriate.

In a preferred embodiment, the stent frame is initially provided as a circular cross-section nitinol tube. The tube is laser cut according to a pattern corresponding to the struts, cells and the like. The cut tube preferably is electrochemically polished to as to remove rough edges. The cut and polished nitinol tube may be shaped in accordance with a desired manner, such as shaping the anchors to extend radially outwardly, and the nitinol stent frame may be heated-treated to both establish the shape memory and to obtain desired elasticity attributes.

With specific reference next to FIG. 5, an embodiment of a replacement heart valve 160 is illustrated in which the valve body 30 of FIGS. 1-3 is disposed on the stent frame 90 of FIG. 4. In this embodiment, the skirt portion 40 of the valve body 30 is disposed on the outside of the stent 90 and the leaflet portion 50 is disposed on the inside of the stent 90. The downstream ring 76 and leaflet supports 80 are attached to the stent 90. Apertures 162 are formed through the skirt 40 as appropriate to accommodate the anchors 150, 154. The anchors 150, 154 and corresponding apertures 162 are configured so that when the stent 90 is compacted, the anchors still extend through the apertures. More specifically, when the stent 90 is compacted and the foreshortening portion 110 lengthens, the anchors 150, 154 move within the corresponding apertures 162, but the anchor tips 152, 156 do not exit the apertures 162.

In one embodiment, during manufacture, the skirt portion 40 is attached to the stent 90 before any portion of the leaflet portion 50 is attached to the skirt portion 40. In some embodiments, the skirt portion 40 is fit over the stent 90 prior to folding the leaflet portion 40. In other embodiments, the stent is slid between the leaflet portion and skirt portion after they are folded. After the stent 90 is sandwiched between the leaflet portion 50 and skirt portion 40, the leaflets 54 are attached to the leaflet supports 80 and the commissural tabs 60 are attached to the downstream ring 76. In some embodiments, such attachments are made such that at least portions of the valve body can move relative to the stent while the stent is foreshortening.

In another embodiment, the skirt portion 40 of the valve body 30 is attached to the outside of the stent 90, and the stent and valve body are compressed into the compacted state without the leaflet portion 50 being folded relative to the skirt portion 40. As such, the leaflet portion 50 is not in contact with or directly connected to the stent 50. During a procedure to deploy the replacement valve into a patient, the partially-completed assembly is advanced into place and the stent is expanded so that the anchors grasp the patient's native annulus. The leaflet portion 50 of the valve is then folded over and into the stent 90, and is then attached, while in place, to the skirt portion 40.

Figure 6A:
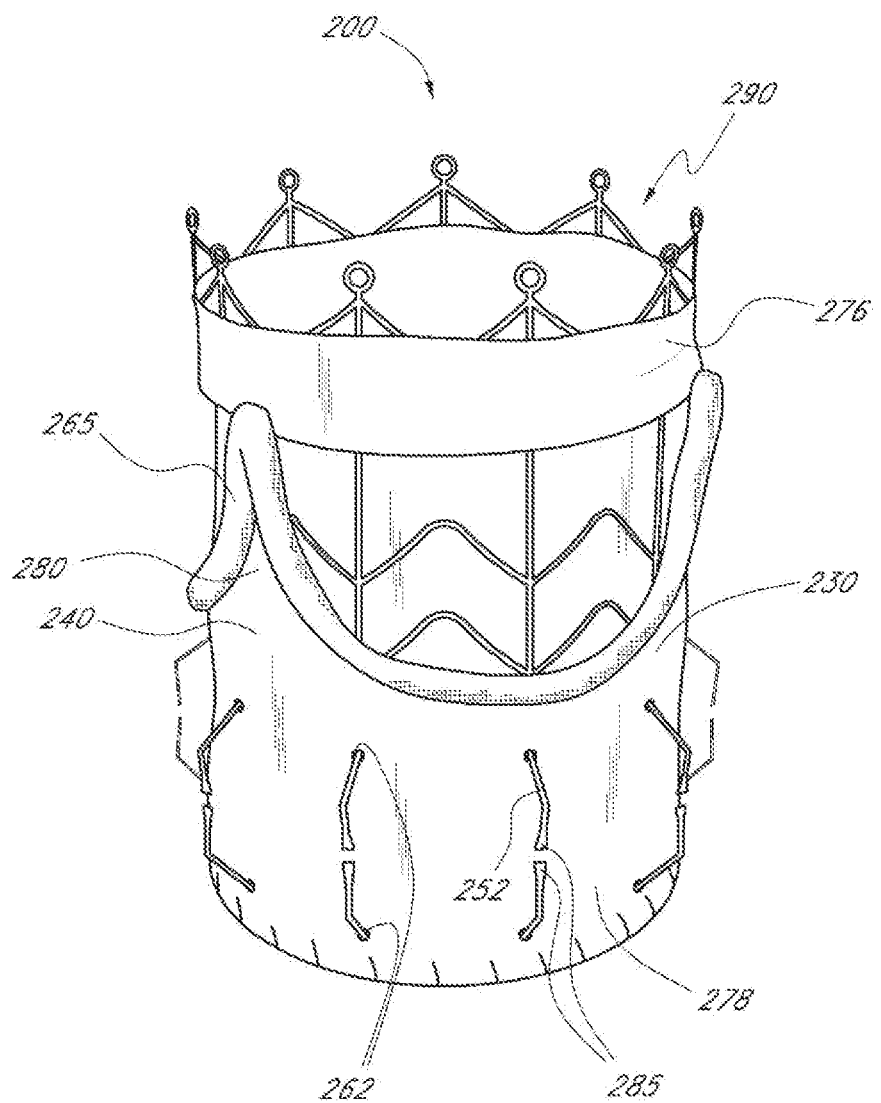
FIG. 6A is a side perspective view of another embodiment of a heart valve comprising a tissue valve body mounted on a stent frame.
Figure 6B:
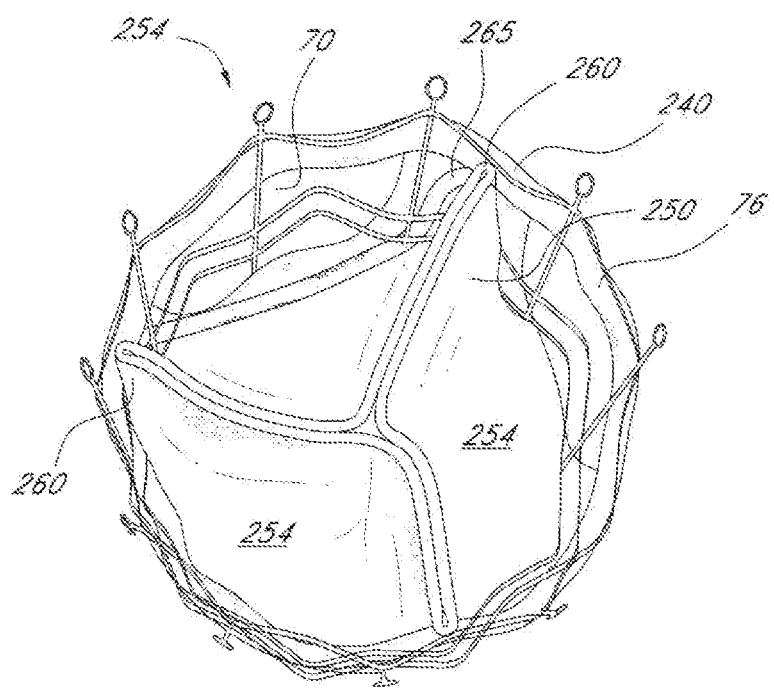
FIG. 6B shows the heart valve of FIG. 6A in a closed condition and viewed from a downstream position.
Figure 6C:
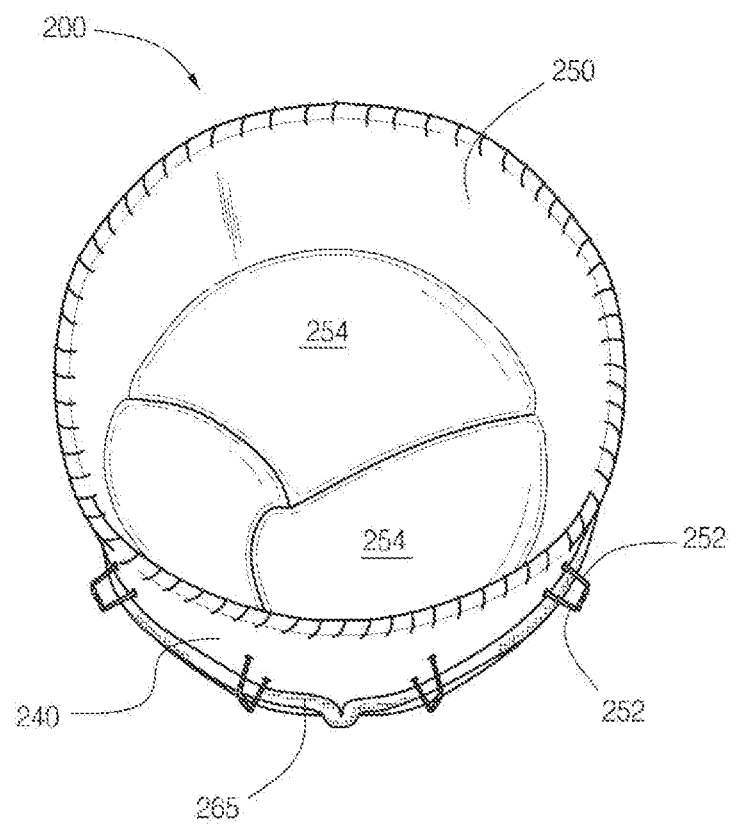
FIG. 6C shows the heart valve of FIG. 6A in a closed condition and viewed from an upstream position.

With reference next to FIGS. 6A-C, another embodiment of a heart valve 200 is illustrated in which a stent frame 290 is sandwiched between an inner layer 250 and an outer layer 240 of a valve body 230. In preferred embodiments the valve body 230 is formed of a single piece of tissue wrapped about the stent frame 290 so that the skirt portion 240 is the outer layer and sits on and is attached to the outside of the stent 290. The leaflet portion 250 is the inner layer. It sits within the interior of the stent 290 and is attached to the skirt portion 240. In the illustrated embodiment, first and second side edges 264, 266 of leaflets 254 are tightly sutured to first and second side edges 272, 274, respectively, of leaflet support portions 280. Commissural tabs 260 of the leaflet portion 250 are attached to a downstream ring 276 of the skirt portion 240. In this arrangement, the connection between the leaflet portion 250 and the skirt portion 240 securely holds onto the stent 290, but also prevents leaks. Further, the downstream ring 276, to which the commissural tabs 260 are attached, helps to distribute forces exerted on the commissural tabs during valve closure.

Stent anchors 250, 254 in the embodiment illustrated in FIGS. 6A-C extend through aperture 262 in an upstream ring 278 of the valve body 230. In the illustrated embodiment, the stent anchors 250, 254 have a widened portion 285 towards their tips 252, 256. As such, during elongation of a foreshortening portion 210 of the stent 290 in which the anchors 250, 254 are drawn apart from each other, the enlarged portions 285 of the anchors help prevent the tissue valve body 230 from slipping off the anchors or, more specifically, prevent from the anchor tips 252, 256 from slipping through their associated apertures 262.

In additional embodiments, a valve body 230, 30 as depicted in FIGS. 6A-C or as in FIGS. 1-4 can be mounted to a stent frame that does not foreshorten upon expansion. As in embodiments above, the skirt 40, 240 can be disposed on the outside of the stent frame, and the leaflet portion 50, 250 is inverted and folded so as to be within the stent frame, but aligned with the skirt portion. The leaflet portion and skirt portion are then sewn together as appropriate so that at least part of the stent frame is sandwiched between the portions. Preferably the valve body material is contiguous at the fold line between the skirt portion and leaflet portion, which is at or adjacent to the upstream end of the heart valve, thus further decreasing the likelihood of paravalvular leaks.

Figure 7:
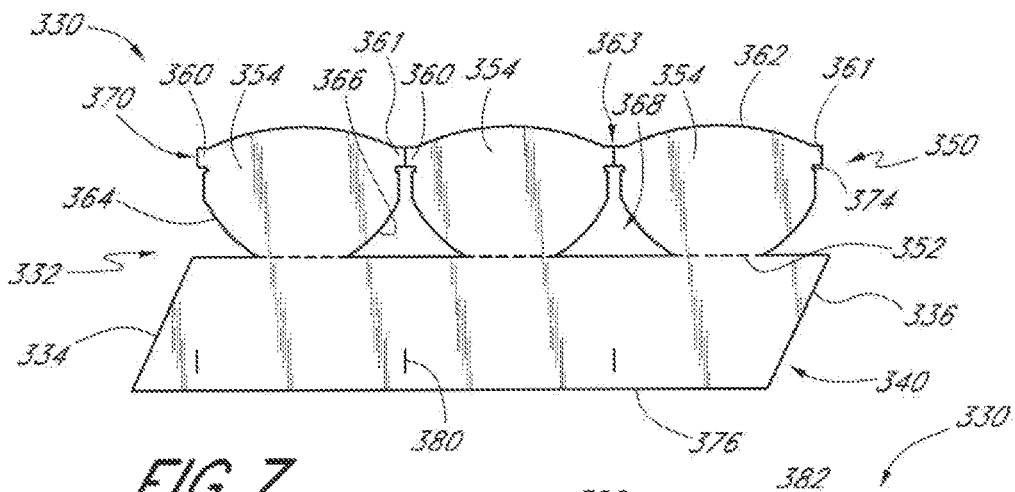
FIG. 7 shows a flat pattern for cutting a flat source tissue to form another embodiment of a valve body.

With reference next to FIGS. 7-9A, another embodiment of a valve body 330 is depicted. FIG. 7 discloses a flat pattern 332 for cutting flat source tissue to assemble into the valve body embodiment. The illustrated valve body pattern 332 has first and second ends 334, 336, and defines a skirt portion 340 and a leaflet portion 350. The leaflet portion 350 comprises three leaflets 354, each having a downstream leaflet edge 362 and opposing first and second leaflet side edges 364, 366. An aperture 368 is cut between adjacent leaflets 354 and the cut out tissue removed so as to define the leaflets 354.

Each of the leaflets 354 has a first and a second opposing commissural tab portion 360, 361. In the illustrated flat pattern 332, the commissural tab portions 360, 361 of adjacent leaflets 354 are initially co-formed as a connection 363 between adjacent leaflets. During cutting according to the flat pattern, this commissural connection 363 is cut so as to define the first and second commissural tabs 360, 361 of adjacent leaflets, which first and second commissural tabs 360, 361 have first and second cut ends 370, 371, respectively. In the illustrated embodiment, a relatively small jog, or offset 374, is cut between each leaflet side edge 364, 366 and the adjacent commissural tab 360, 361.

With continued reference to FIG. 7, preferably the skirt portion 340 of the valve body 330 is substantially contiguous, without significant cut-outs such as the windows of the FIG. 1-4 valve body. The skirt 340 has a downstream edge 376, and is connected to the leaflet portion 350 at a fold line 352. In the skirt portion 340, the valve pattern's first and second ends 334, 336 are cut to be diagonal relative to the downstream edge 376, which preferably is parallel to the fold line 352. In the illustrated embodiment, commissural slits 380 are cut into the skirt portion 340 so as to be generally aligned with the cut edges 370, 371 of adjacent first and second commissural tabs 360, 361.

Figure 8:
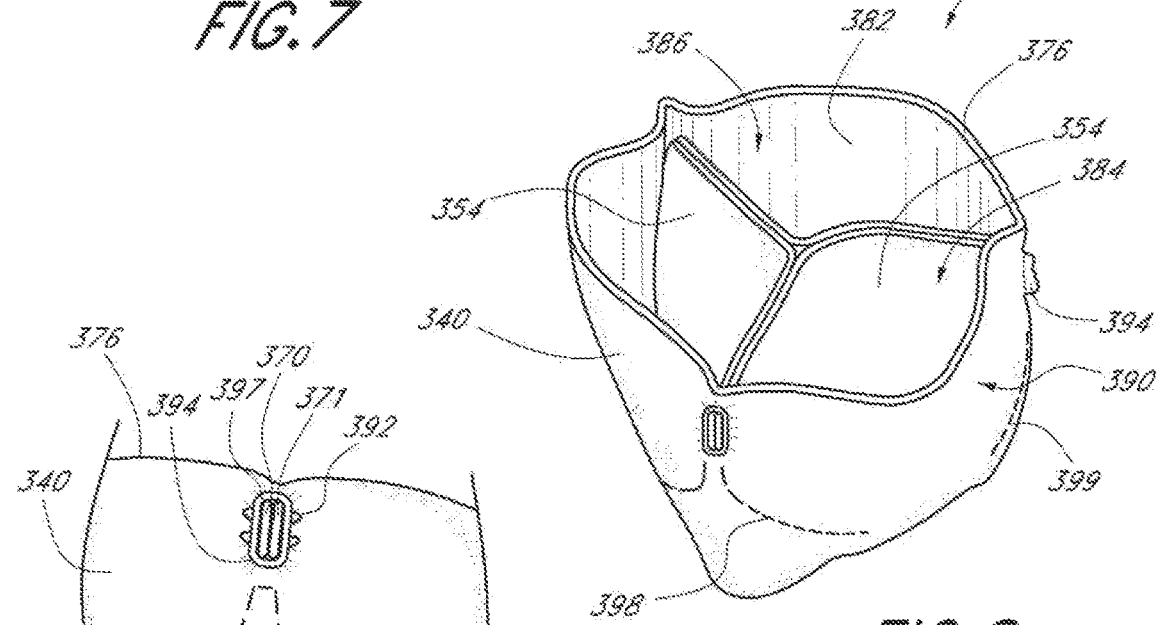
FIG. 8 shows a perspective view of a valve body constructed of tissue cut according to the pattern of FIG. 7.

With specific reference next to FIG. 8, the valve body 330 is constructed by folding the skirt portion 340 relative to the leaflet portion 350 along the fold line 352, and securing the diagonal ends 334, 336 of the skirt portion 340 together to establish the tubular shape of the valve body 330. In this arrangement, an inner surface 382 of the skirt portion 340 faces outer surfaces 384 of the leaflets 354, and an interior 386 of the valve body 330 is defined by the inner surface 382 of the skirt portion 340. Inner surfaces of the first and second commissural tab portions 360, 361 of adjacent leaflets 354 are engaged with one another, and the engaged tabs 360, 361 are passed through the corresponding commissural slit 380 of the skirt portion 340. With specific reference also to FIG. 9A, which is a close-up view taken from outside the skirt portion, the engaged first and second commissural tab portions 360, 361 are arranged so that their cut ends 370, 371 are facing generally radially outwardly and are adjacent the outer surface 390 of the skirt portion 340.

The engaged commissural tab portions 360, 361 are connected to one another, preferably by sutures 392. In the illustrated embodiment, a slit edge portion 394 immediately surrounding the slit 380 is made to engage the outer surfaces 396 of the commissural tabs 360, 361 so that a cut edge 397 of the slit 380 faces radially outwardly as do the cut ends 370, 371 of the tabs 360, 361. The slit edge portion 394 and engaged commissural tabs 360, 361 then are all sewn together as shown in FIG. 9A.

In the illustrated embodiment, the inner surface 382 of the skirt 340 in the slit edge portion 394 engages an outer surface of the tabs 360, 361. In still other embodiments, the engaged commissural tabs 360, 361 are first sewn-together on the outside of the skirt 340, and the sewn-together commissural tabs 360, 361 are then sewn onto the tissue surrounding the slit 380. In another embodiment, the engaged commissural tabs 360, 361 are not sewn to one another. Instead, each tab is folded adjacent its cut edge 370, 371 to engage the outer surface 390 of the skirt portion 340 adjacent the slit 380, and is then sewn to the skirt. In another such embodiment the engaged portion of the commissural tabs 360, 361 can also be sewn together, or held together by clips or the like.

Figure 9A:
FIG. 9A is a close-up view of a side of the valve body of FIG. 8.
Figure 9B:
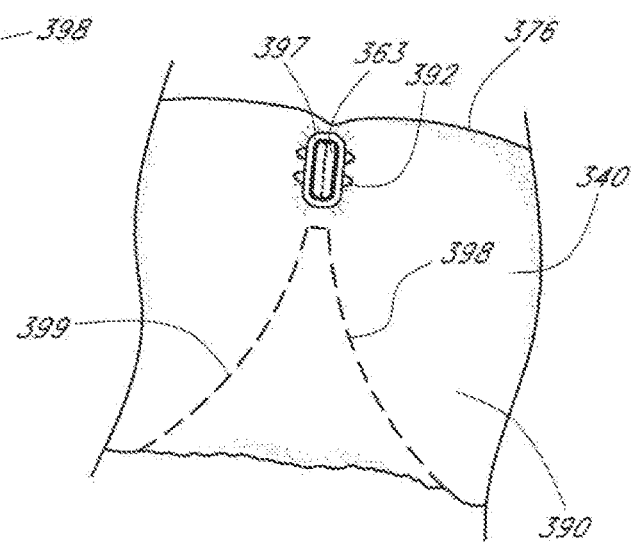
FIG. 9B is a close-up view as in FIG. 9B but showing features of another embodiment.

With continued reference to FIGS. 7-9A, the first and second leaflet side edges 364, 366 are also sewn to the skirt portion 340. As such, a good seal is sewn between the leaflets 354 and the skirt portion 340 so as to prevent any blood leakage therebetween during operation of the valve. FIGS. 9A and B show first and second seams 398, 399 that attach the leaflets 354 to the skirt along the first and second leaflet side edges 364, 366.

The offset 374 between the leaflet side edges 364, 366 and the tabs 360, 361 facilitates a clean transition between the tabs, which extend through the commissural slit 380, and the leaflet side edges, which are sewn to the inner surface 382 of the skirt portion 340. Preferably the leaflet edge in the offset 374 also engages the skirt.

The valve body 330 can be sewn together in several ways. In another embodiment, the commissural slits 380 can be used as a guide during folding of the leaflet portion 350 over the skirt portion 340, and the operator is careful to make sure the leaflets 391 are properly aligned. In another embodiment, prior to forming the valve body into a tube, but after folding, at least one and preferably at least two of the leaflets 354 are sewn onto the skirt 340. Sewing the leaflets onto the skirt when still in a flattened state can be more convenient. This method also enables reliable placement of the leaflets 354 in the correct position relative to the skirt 340, and maintenance of them in a correct placement during suturing. Also, since at least one of the leaflets is already sewn securely in place before the valve body 330 is formed into a tube by connecting the first and second skirt ends 334, 336, the previously-connected leaflet or leaflets function as a guide and reference point to assist in proper placement and sewing of the remaining leaflet(s).

Of course, in other embodiments, the valve body 330 can be rolled into a tube prior to folding and/or prior to attaching the leaflets 350 to the skirt portion 340. For example, in one embodiment the commissural tabs 360, 361 are attached and put in place once the valve body 330 is rolled into a tube. Once secured in place, the tabs 360, 361 serve as a guide to help maintain the leaflets 354 in a correct position while they are attached to the skirt 340.

In another embodiment, a valve body 330 is provided having a structure substantially as in the valve body of FIGS. 7 and 8, except that the commissural connection 363 between adjacent leaflets 354, which in FIG. 7 is cut to form opposing commissural tabs 360, 361, is not cut, but instead remains as a commissural tab 363 connecting adjacent leaflets 354. Such an embodiment can be constructed substantially as described above; however, only the commissural tabs 360, 361 at the first and second pattern ends 334, 336 have cut edges 370, 371 so as to be constructed as shown in Figure A.

With specific reference to FIG. 9, in an embodiment having a contiguous commissural tab 363 between the leaflets 354, each tab 363 preferably is folded so that inner surfaces of the tab 363 are engaged. The folded tab 363 is passed through the corresponding commissural slit 380. Each folded commissural tab 363 is sutured to the skirt portion 340, preferably in a manner similar to the embodiments discussed above.

With reference next to FIG. 10, another embodiment of a flat pattern 432 for cutting a valve body 430 from a flat source tissue is illustrated. In this embodiment, the valve body 430 is divided into a skirt portion 440 and a leaflet portion 450. The leaflet portion 450 comprises three leaflets 454, each having a curved downstream leaflet edge 462 and curved first and second side edges 464, 466. Opposing first and second commissural tab portions 460, 461 are also defined on each leaflet 454. In the illustrated pattern, the commissural tab portions 460, 461 and side edges 464, 466 are formed by removing tissue between the leaflets 454, including between adjacent first and second tab portions of adjacent leaflets. Three commissural slots 480 are cut through the skirt portion 440 generally corresponding to the placement of the commissural tabs 460, 461. The slots 480 of the illustrated embodiment are formed by cutting and removing a portion of tissue, as opposed to simply cutting a slit as in some other embodiments. Once cut from source tissue, the valve body 430 can be constructed in a manner sharing similarities with the valve body 330 of FIGS. 7-9.

Figure 11:
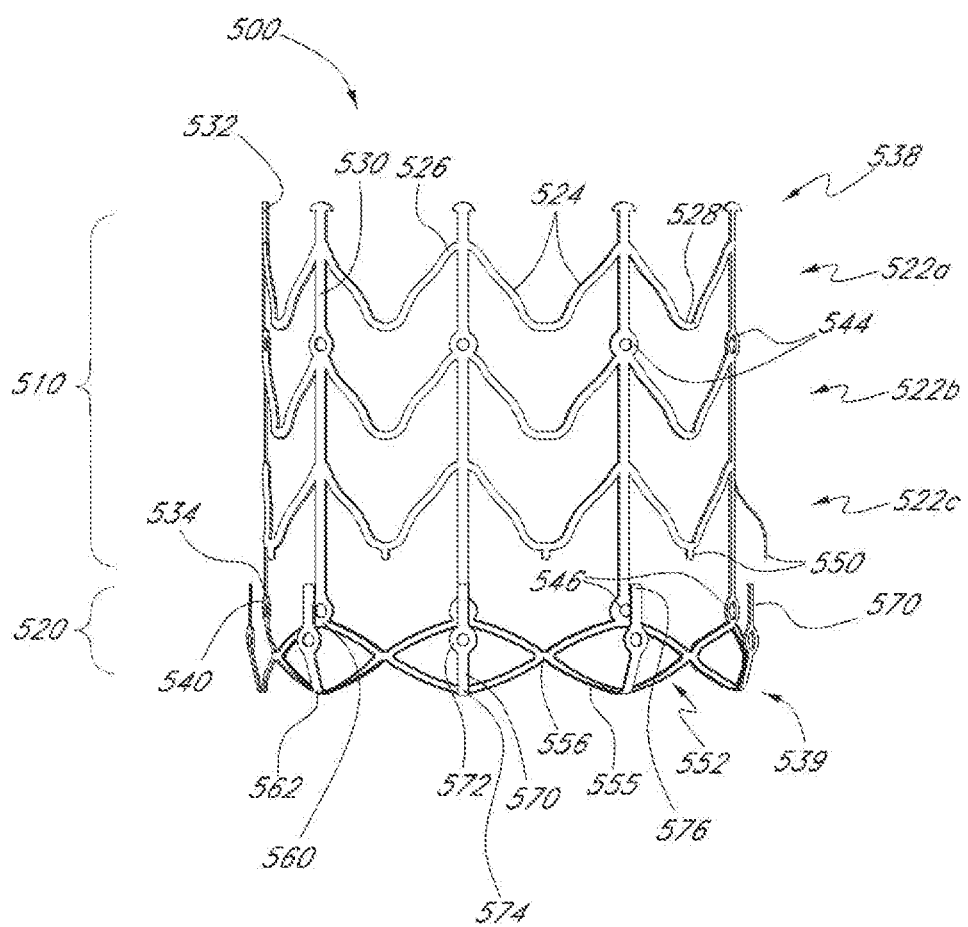
FIG. 11 is a schematic side view of another embodiment of a stent frame for supporting a heart valve body.

With reference next to FIG. 11, another embodiment of a stent frame 500 is illustrated. In the illustrated embodiment, the stent frame 500 comprises a non-foreshortening portion 510 and a foreshortening portion 520. The non-foreshortening portion 510 comprises three rings 522a-522c of undulating circumferentially expansible struts 524 that connect to one another at apices 526, 528. Longitudinal struts 530 have first and second ends 532, 534, and extend from a first end 538 toward a second end 539 of the stent 500 but terminate at a transition 540 from the non-foreshortening portion 510 to the foreshortening portion 520. The apices that intersect with the longitudinal struts 530 are referred to as "connected" apices 526, and apices between connected apices 526 are referred to as "free" apices 528.

In the illustrated embodiment, a first ring 522a is disposed adjacent the first end 538 of the stent and a second ring 522b is disposed adjacent the first ring 522a. A set of first eyelets 544 are formed at the connected apices 526 of the second ring 522b. A set of second eyelets 546 are also formed at the second ends 534 of each longitudinal strut 530, which in the illustrated embodiment is also the transition 540. In a third ring 522c, the free apices 528 each comprise a protuberance 550 extending therefrom, which protuberance can also be referred to as an apical anchor 550. Preferably the struts 524 in the third ring 522c are pre-shaped so as to flare radially outwardly when the stent frame 500 is in an expanded state as shown in FIG. 11.

With continued reference to FIG. 11, the foreshortening portion 520 of the illustrated stent frame 500 comprises a ring 552 of generally diamond-shaped cells 555 connected to one another at connectors 556. A first end 560 of each cell 555 is connected to the non-foreshortening portion 510 at the second eyelets 546. As in embodiments discussed above, the foreshortening cells 555 are configured so that as the stent frame 500 is radially compacted, the foreshortening portion 520 of the stent becomes longitudinally longer and, correspondingly, when the stent frame is expanded radially, the foreshortening portion 520 shortens.

A second end 562 of each cell 555 in the foreshortening portion 520 is attached to an anchor 570 that extends generally radially outwardly and toward the first end 538 of the stent. An anchor eyelet 572 is formed in each anchor 570, preferably between a base 574 and a tip 576 of each anchor 570. During operation, and consistent with other embodiments discussed herein, as the stent 500 in a compacted state is placed at a native heart valve annulus, the compacted stent is first arranged so that the annulus is disposed between the apical anchors 550 and the anchor tips 576. The stent 500 is then allowed to expand, prompting foreshortening, which brings the anchor tips 576 closer to the apical anchors 500 and grasps the native annulus therebetween. In the illustrated embodiment, the apical anchors 500 are not collinearly aligned with the end anchors 570.

Figure 12:
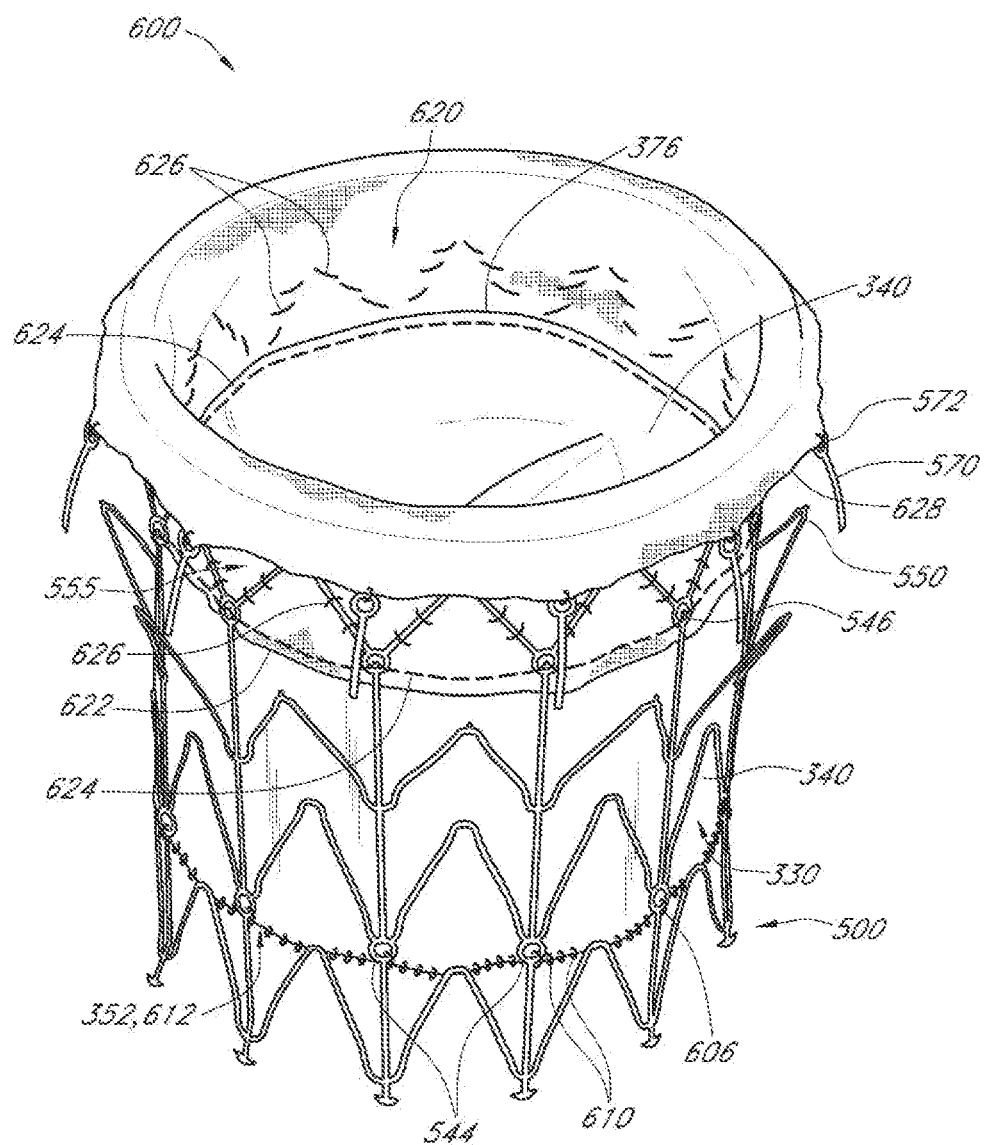
FIG. 12 is a perspective view of the stent frame of FIG. 11 with a heart valve body constructed from source tissue cut in accordance with the pattern of FIG. 10 mounted thereon.
Figure 13:
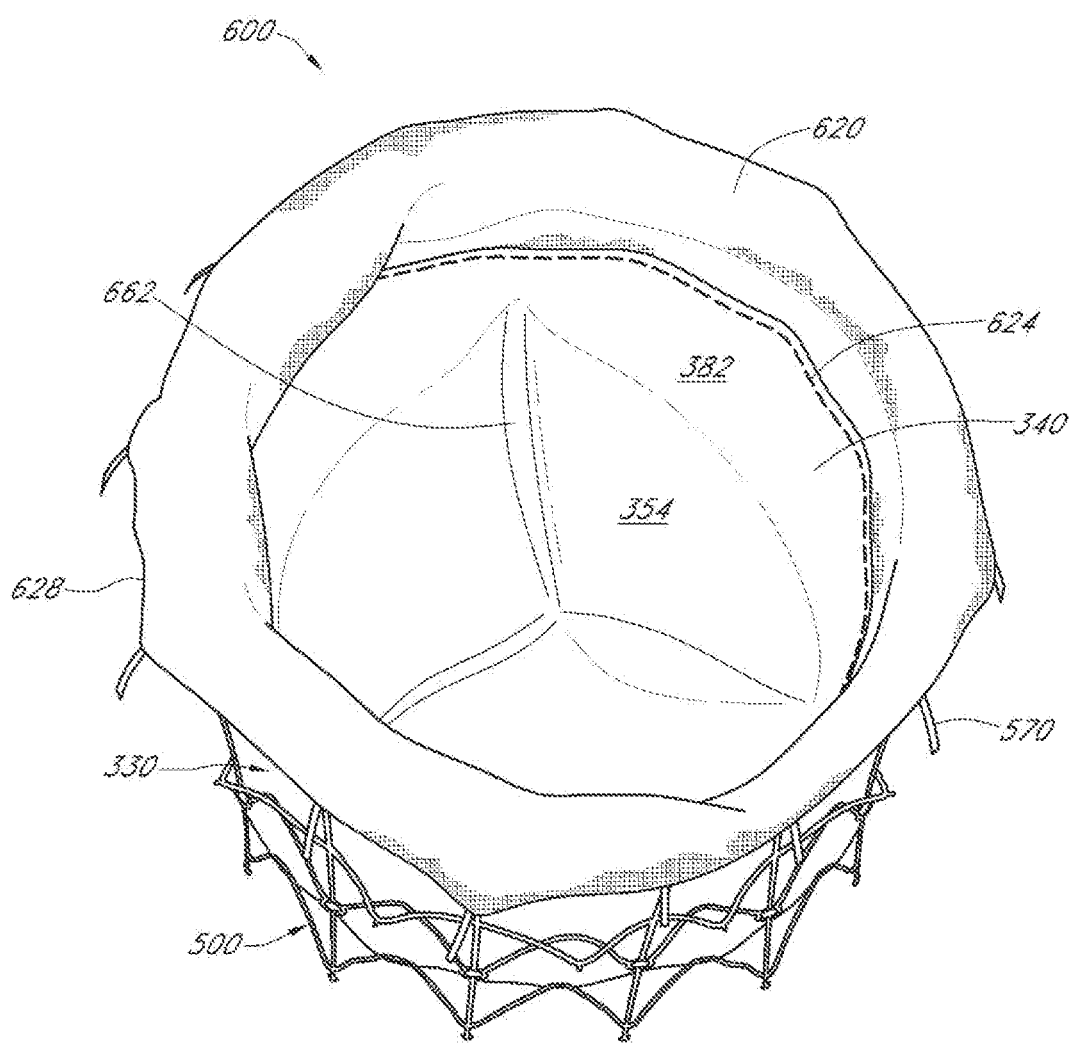
FIG. 13 shows the heart valve of FIG. 12 in a closed condition and viewed from a downstream position.

With additionally reference to FIGS. 12 and 13, an embodiment of a replacement heart valve 600 comprises a valve body 330 as in FIGS. 7-9 attached to a stent frame 500 as in FIG. 11. In this embodiment, however, the entire valve body 330 is disposed inside the stent 500. More specifically, and as illustrated in FIG. 12, the skirt portion 340 of the valve body 330 is sewn to the first eyelets 544 of the stent. In the illustrated embodiment, the fold line 352 of the valve body 330 is hemmed, and certain stitches 606 of a hem seam 610 also engage the first eyelets 544 in the non-foreshortening portion 510 of the stent 500. In this illustrated embodiment, the hemmed fold line 352 becomes an upstream end 612 of the valve body 330.

With continued reference to FIGS. 12 and 13, an elongate tubular portion 620 of flexible, longitudinally expandable fabric is attached to the downstream end 376 of the skirt portion 340 in the illustrated embodiment. More particularly, a first end of the fabric 622 is sewn to the downstream end 376 of the skirt portion about the circumference of the skirt portion by a downstream seam 624. Also, the fabric 620 preferably is connected to the outer surface of the skirt 340, and is also sewn onto the second eyelets 546 of the stent frame 500. Preferably, the fabric 620 is also sewn to the foreshortening cells 555 at several points by connector stitches 626.

In the illustrated embodiment, the fabric 620 curves around the second end 539 of the stent frame 500, generally following the curvature of the downstream anchors 570. Second end 628 of the fabric portion 620 is sewn to the anchor eyelets 572. Preferably, the flexible fabric 620 is sufficiently expandable to move with the foreshortening portion 520 as the stent 500 moves between the compacted state and the deployed, relaxed expanded state. As such, in the illustrated embodiment, the tissue valve body 330 is confined to the non-foreshortening portion 510 of the stent and the flexible fabric 620 spans the foreshortening portion 520 of the stent. Thus, the tissue valve body 330 is not subject to longitudinal expansion and contraction with the stent 500.

In the illustrated embodiment, the tissue portion of the valve body 330 is sewn directly to the stent frame 500 at only the upstream end 612. The downstream edge 376 of the skirt portion 340 is attached to the fabric 620, which fabric is sewn directly to the stent 500 at the second eyelets 546 via the downstream seam 624. In another embodiment, the same seam 624 that connects the fabric 620 to the skirt 340 also connects the skirt 340 to the second eyelets 546.

With continued reference to FIGS. 7-9 and 11-13, the illustrated embodiment of an assembled heart valve 600 comprises two layers of tissue, preferably formed from a single, contiguous piece of tissue. The leaflet portion 350 of the valve, which includes the leaflets 354, is sewn directly only to the skirt portion 340. As such, during valve operation between open and closed states, the leaflet portion 350, and specifically the leaflets 354, directly engages only the skirt portion 340. In turn, the skirt portion 340 is attached to and interacts with the stent 500 and other materials such as the downstream fabric portion 620.

It is to be understood that, in other embodiments, a portion or all of what has been shown as the fabric portion 620 in the embodiment illustrated in FIGS. 12 and 13 can be replaced by providing a longer skirt portion of the tissue valve portion. It is also to be understood that, in additional embodiments, the illustrated valve body 330 can be used with a non-foreshortening stent.

Figure 14:
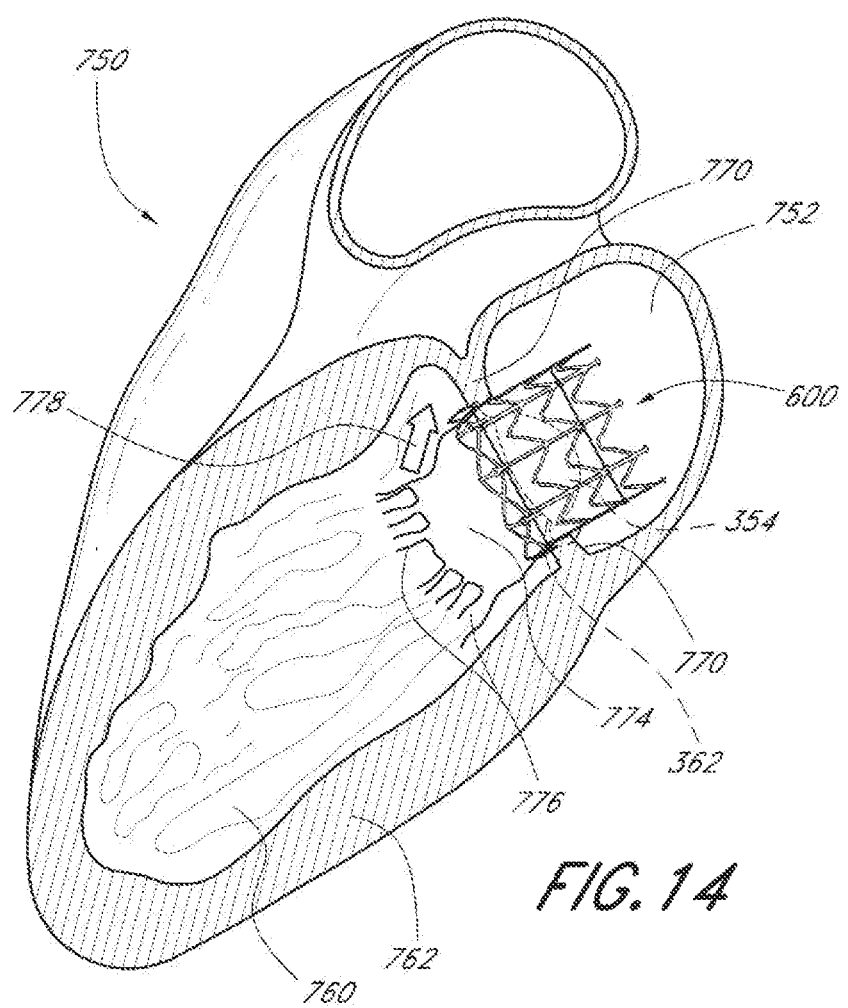
FIG. 14 shows the heart valve of FIG. 12 placed in a mitral annulus of a human heart in accordance with one embodiment.

With reference next to FIG. 14, a schematic representation of the heart valve 600 as discussed above in connection with FIGS. 12 and 13 is depicted installed in a human heart 750. The heart is shown in cross-section, and represents typical anatomy, including a left atrium 752 and left ventricle 760. The left ventricle 760 is defined by a muscular wall 762. The left atrium 752 and left ventricle 760 communicate with one another through a mitral annulus 770. Also shown schematically in FIG. 14 is a native anterior mitral leaflet 774 having chordae tendineae 776 that connect a downstream end of the anterior mitral leaflet 774 to the muscle wall 762 of the left ventricle 760. A left ventricle outflow tract 778 extends toward the top of the left ventricle 760.

As shown in FIG. 14, the valve 600 of FIGS. 12-13 is disposed so that the mitral annulus 770 is grasped between the anchors 570 and apical anchors 550 in accordance with a method of aligning and deployment of the stent 500 discussed previously. As such, all or most of the stent 500 extends into the left atrium. The portion of the stent 500 disposed upstream of the annulus 770 can be referred to as being positioned supra-annularly. The portion generally within the annulus 770 is referred to as positioned intra-annularly. The portion downstream of the annulus is referred to as being positioned sub-annularly. In the illustrated embodiment, only a part of the foreshortening portion is positioned intra-annularly or sub-annularly, and the rest of the stent 500 is supra-annular.

In the illustrated embodiment, the anterior mitral leaflet 774 has not been removed prior to deploying the replacement valve 600. Preferably, the posterior mitral leaflet (not shown) also has not been removed prior to deploying the replacement valve. However, in other embodiments, one or both of these natural valve leaflets may be removed before deploying the replacement valve.

With the stent 500 placed mostly supra-annularly within the left atrium 752, the stent 500 does not interfere with left ventricle function during pumping. More specifically, the stent 500 does not interfere with blood flow from the left ventricle 760 through the outflow tract 778 and does not interfere with deformation of the left ventricle 760 as the muscle wall 762 contracts during pumping. In the illustrated embodiment, the valve body 330 is attached to the stent 500 so that the downstream edges 362 of the valve are generally within the mitral annulus 770. This is referred to as intra-annular placement of the valve body 330.

Figure 15:
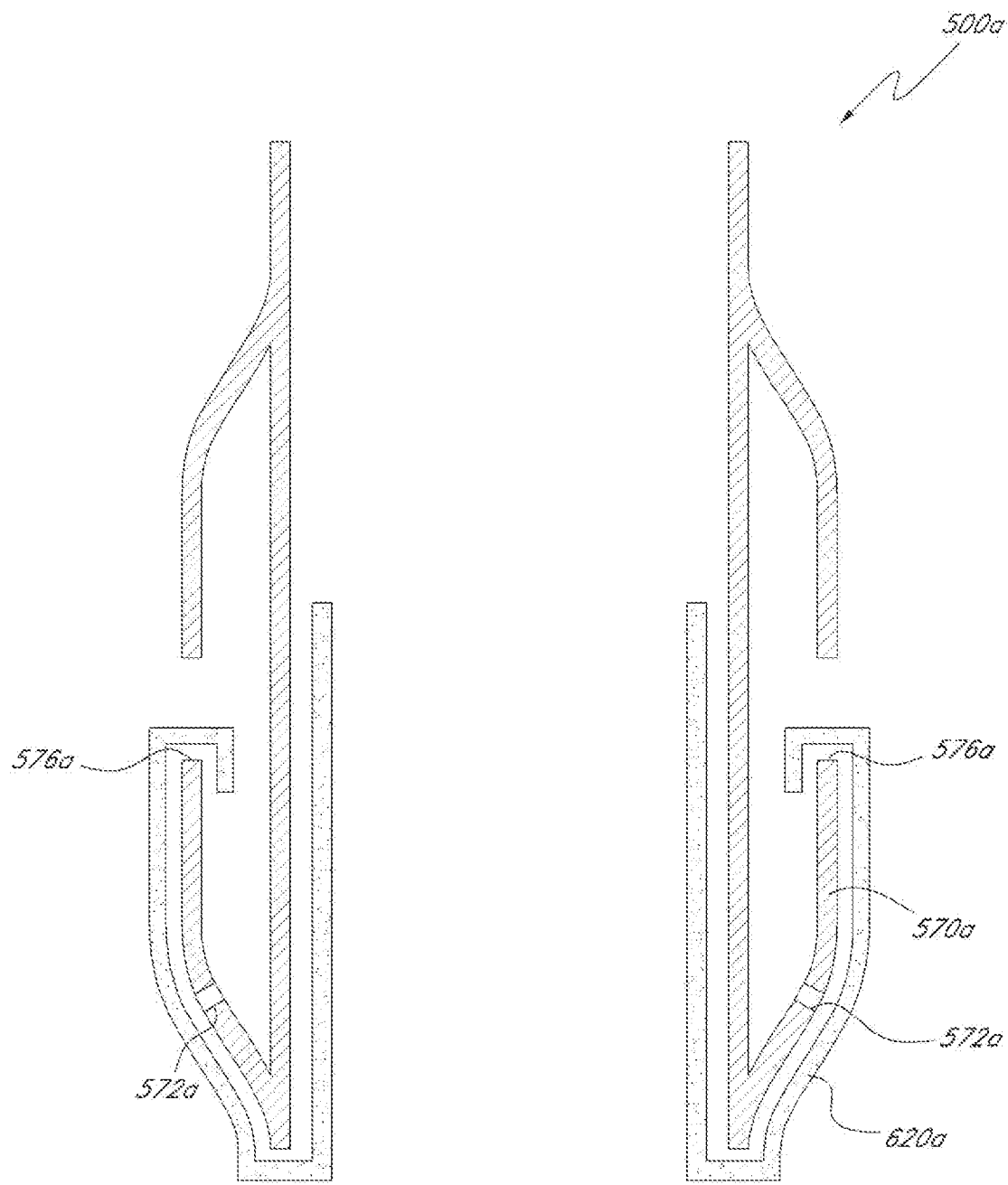
FIG. 15 is a schematic side section view showing opposing walls of a heart valve stent frame similar to that of FIG. 11 and schematically showing placement of an expandable fabric portion on the stent in accordance with another embodiment.

With reference next to FIG. 15, a schematic cross-sectional side view schematically showing a portion of a stent 500a and fabric portion 620a of another embodiment. This embodiment is similar to that of FIGS. 12 and 13, except that the fabric portion 620a extends beyond anchor eyelets 572a and up to anchor tips 576a. Preferably the fabric 620a is wrapped about the anchor tips 576a and secured in place with a seam around the circumference of the fabric 620a so as to form a generally contiguous band at the tips 576a of the anchors 570a. As such, each anchor 570a will contact the native valve annulus through the fabric 620a.

Figure 16A:
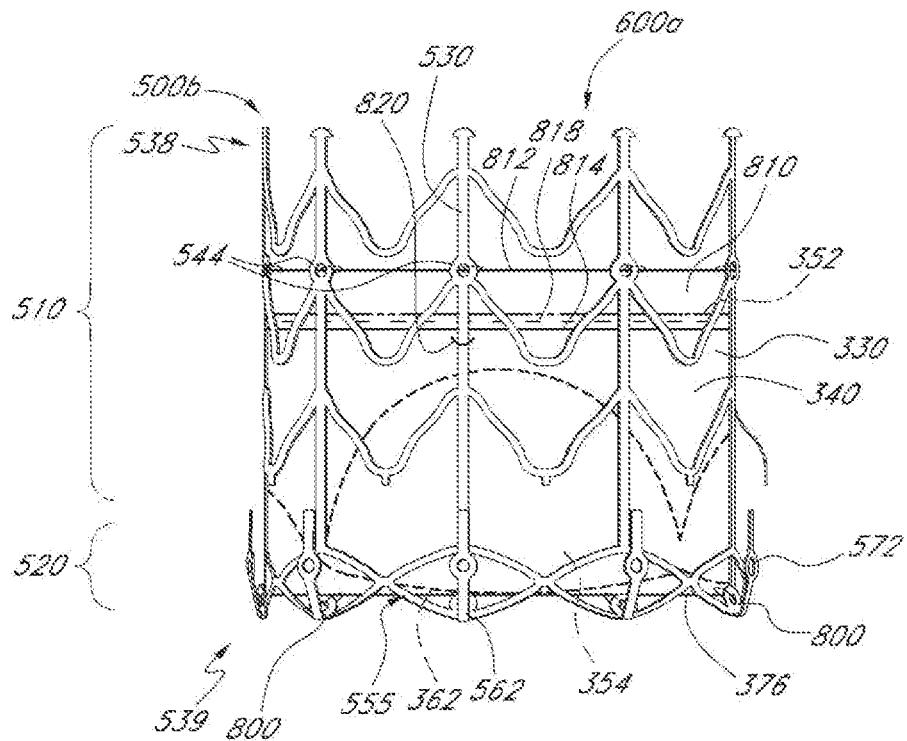
FIG. 16A is a side view of another embodiment of a heart valve, showing the valve body of FIG. 8 mounted onto a stent in accordance with another embodiment.

With reference to FIG. 16A, another embodiment of a heart valve 600a is shown. The illustrated heart valve 600a employs a valve body 330 as discussed above in connection with FIGS. 7-9 mounted on a stent 500b that, for demonstration purposes, is mostly similar to the stent 500 of FIGS. 11-13. As indicated in FIG. 16A, stent 500b, being almost the same as stent 500, includes most of the same structure and uses the same reference numbers. Such structure is described in connection with the discussion of stent 500 above.

In the illustrated stent 500b, a plurality of distal eyelets 800 are provided at the downstream end 539 of the stent 500b, which is also the second end 562 of cells 555 in the foreshortening portion 520 of the stent 500b. In this embodiment, the valve body 330 is attached to the stent 500b so that the downstream edge 376 of the skirt portion 340 is connected to the downstream eyelets 800, such as by sutures. As such, the leaflets 354, and particularly the downstream edges 362 of the leaflets 354, are arranged at, adjacent, or in some embodiments downstream of, second end 539 of the stent 500b.

With continued reference to FIG. 16A, an elongate tubular flexible portion 810, having opposing first and second ends 812, 814, is attached to the valve body 330. More specifically, the second end 814 of the flexible portion 810 is attached to the upstream end 352 of the skirt 340, preferably with a circumferential stitch 818. The first end 812 of the flexible portion 810 is attached to the stent 500b at the first eyelets 544. Preferably, the upstream end 352 of the valve body 330 is not directly attached to the stent 500b, but is only attached to the flexible portion 810, which in turn is attached to the stent 500b.

Preferably the flexible portion 810 is constructed of a flexible material that can increase and decrease in length as the length of the stent 500b increases and decreases due to foreshortening during radial compaction and expansion. Also, preferably the valve body 330 is constructed of a material such as pericardium, which is flexible yet not substantially longitudinally stretchable. To the extent the valve body is made with a material that stretches, preferably the flexible portion 810 is more amenable to longitudinal stretching than the valve body 330 so that as the length of the stent 500b increases, the flexible portion 810, rather than the valve body 330, will stretch longitudinally, and vice versa.

Figure 16B:
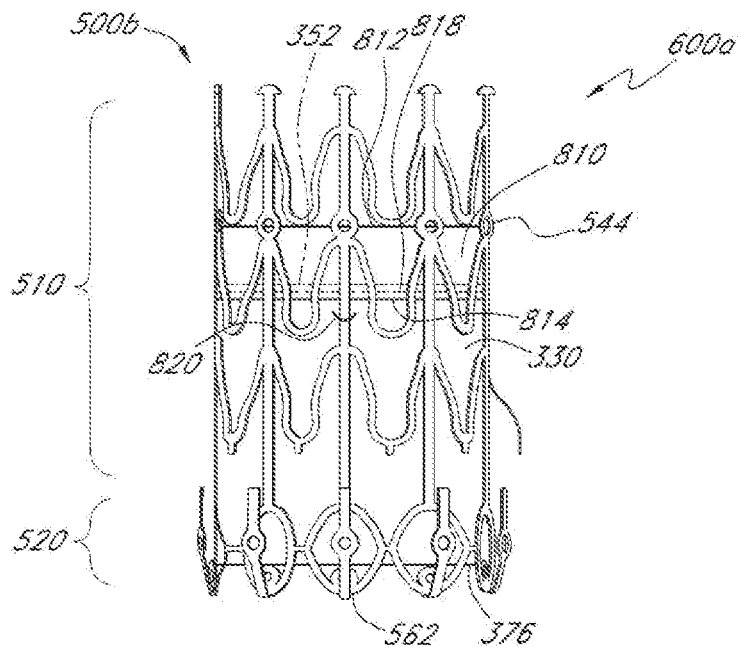
FIG. 16B is a side view of the assembly of FIG. 16A shown in a compacted state.

With additional reference to FIG. 16B, it is noted that in the illustrated embodiment, a portion of the valve body 330 spans the foreshortening portion 520 of the stent. The longitudinally stretchable flexible portion 810, however, is disposed in the non-foreshortening portion 510 of the stent 500b. As the assembled valve 600a is compacted from the expanded portion shown in FIG. 16A to the compacted state shown in FIG. 16B, the foreshortening portion 500 becomes longer. Since the valve body 330 does not stretch substantially, and instead the flexible portion 810 stretches substantially during such lengthening, the stent 500b moves longitudinally relative to the valve body 330. Such a "floating valve body" configuration enables placement of the valve body over at least a portion of the foreshortening portion 520 of the stent 500b without stretching the valve body during lengthening of the foreshortening portion of the valve during the compaction and expansion process.

In the embodiment illustrated in FIGS. 16A and B, at least part of the skirt 340, preferably at or adjacent the upstream end, is loosely attached to one or more longitudinal struts 530 of the stent 500b in a manner that accommodates the floating, longitudinal movement of the valve body 330 relative to the stent 500b upon compaction and expansion, such as by one or more loose stitches 820. In other embodiments, such loose stitches 820 can be in the flexible portion adjacent the valve body. Preferably the stitches 820 are relatively loose so that as the stent 500b moves between the compacted and expanded states, each stitch 820 slides longitudinally over the corresponding longitudinal strut 530. Such stitches 820 are strategically placed so that there is an undisturbed path for the stitch to slide upon.

In the illustrated embodiment, the flexible portion 810 is constructed of a fabric having a sufficiently loose weave and/or material that accommodates longitudinal stretching during compaction, and also takes up the slack as the stent shortens during expansion. It is to be understood, however, that other types of materials and configurations can be employed for the flexible portion. For example, in another embodiment, an elongate tubular portion of pericardium makes up the flexible portion. In this embodiment, preferably the pericardium is creased so as to preferentially fold, accordion style, as the stent shortens during expansion. In another embodiment, the flexible portion comprises a pericardium segment having several fenestrations, which are strategically placed slits that, upon application of longitudinal tension to the pericardium, deform so as to enable the pericardium segment to stretch longitudinally. However, as the stent is expanded and foreshortens, the pericardium recovers to its original shape. After the valve is deployed, and as time passes, tissue in-growth will help to close the fenestrations. In still other embodiments, yet additional structures can be employed. For example, rather than a tubular flexible portion, the flexible portion can comprise an array of elastic cords that attach to the upstream end of the valve body 330, extend longitudinally upon compaction of the valve, and take up the slack as the valve is expanded. Also, although the illustrated embodiment employed the valve body 330, which has two layers, it is to be understood that other embodiments may employ a single-layer valve connected to a flexible portion and mounted on a stent having a foreshortening portion.

Figure 17:
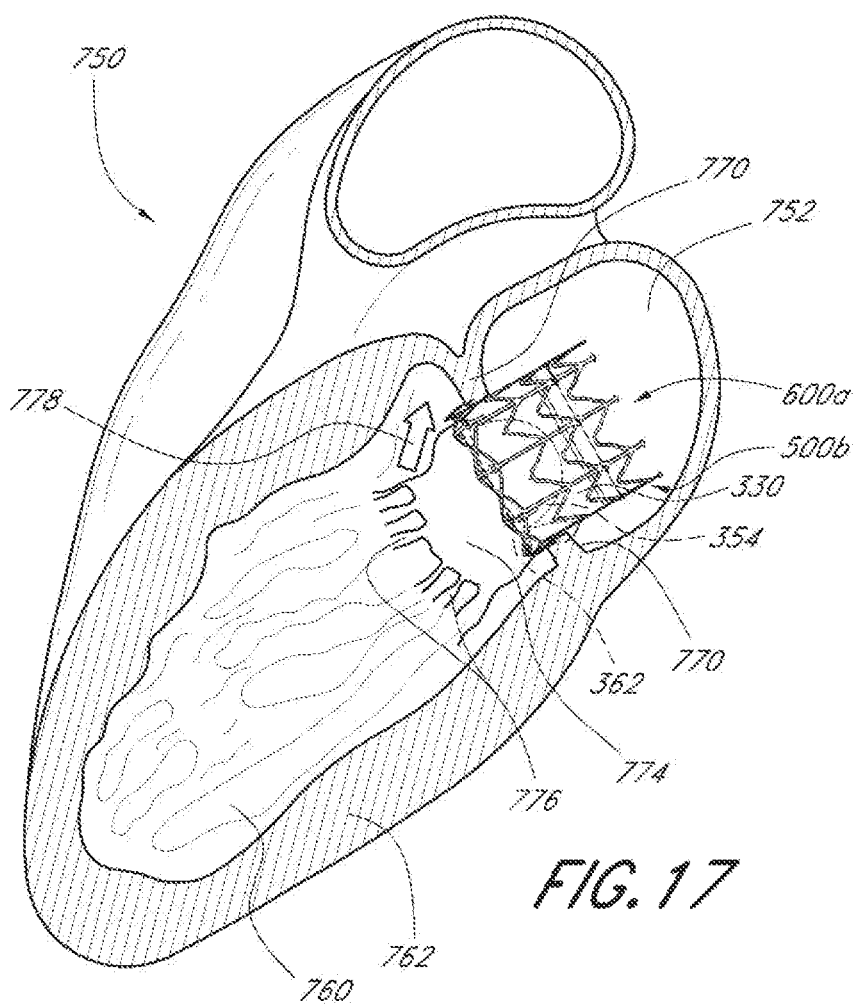
FIG. 17 shows the heart valve of FIG. 16 placed in a mitral annulus of a human heart in accordance with another embodiment.

With reference next to FIG. 17, a schematic representation is made of the valve 600a of FIGS. 16A and B mounted in a human heart. In the illustrated embodiment, the stent 500b is mounted in a manner substantially similar to the stent 500 depicted in FIG. 14. However, the valve body 330 is positioned farther downstream relative to the stent so that the leaflets 354 are generally within the mitral annulus 770, which position can be referred to as intra-annular or partially intra-annular, as the downstream edges 362 of the leaflets 354 may be downstream of the annulus, and thus sub-annular. It is to be understood that, in other embodiments, a valve body can be mounted relative to the stent to be entirely supra-annular, intra-annular, sub-annular, or combinations thereof.

Figure 18:
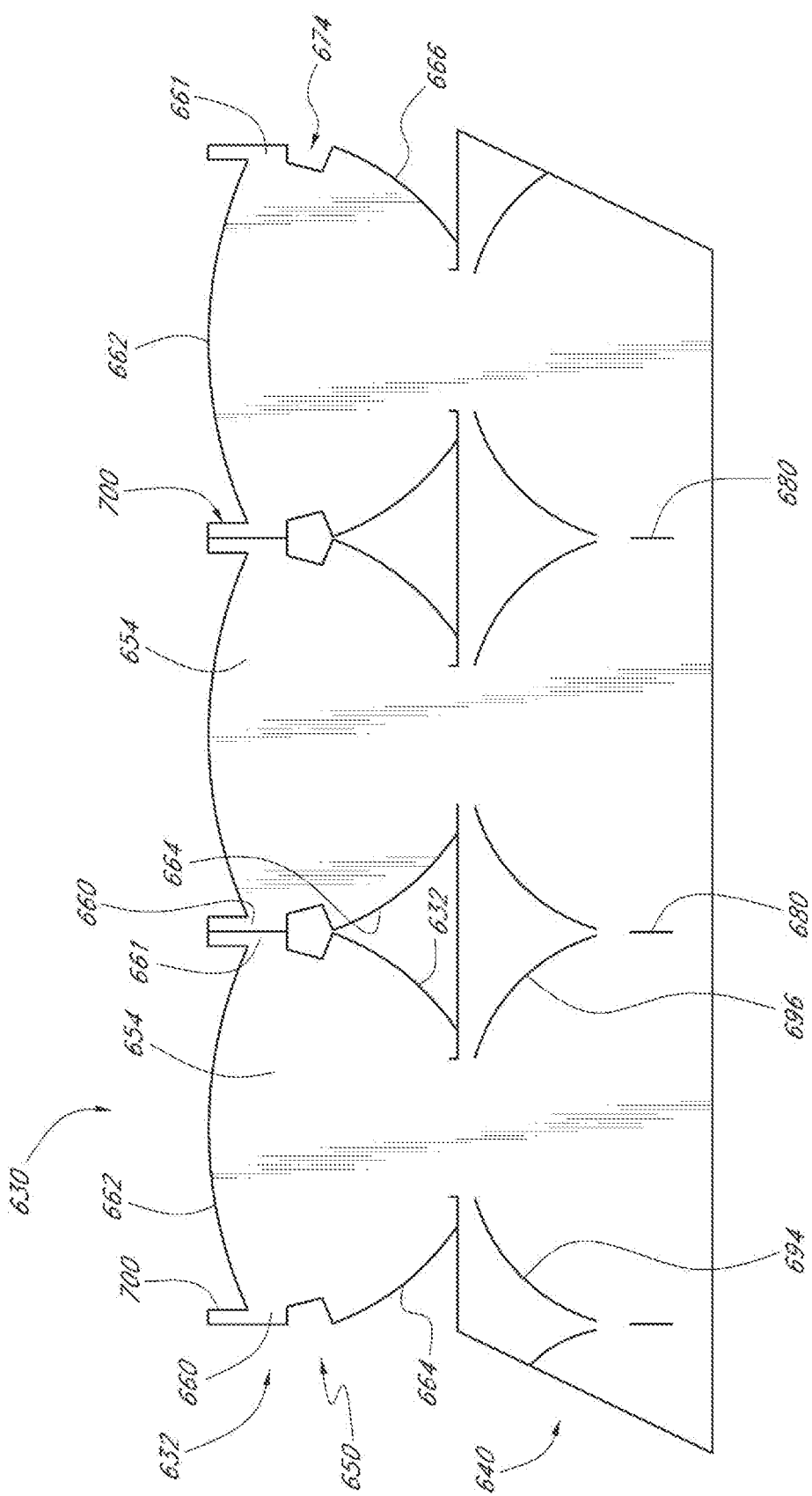
FIG. 18 shows a flat pattern for cutting a flat source tissue to form yet another embodiment of a valve body.
Figure 19:
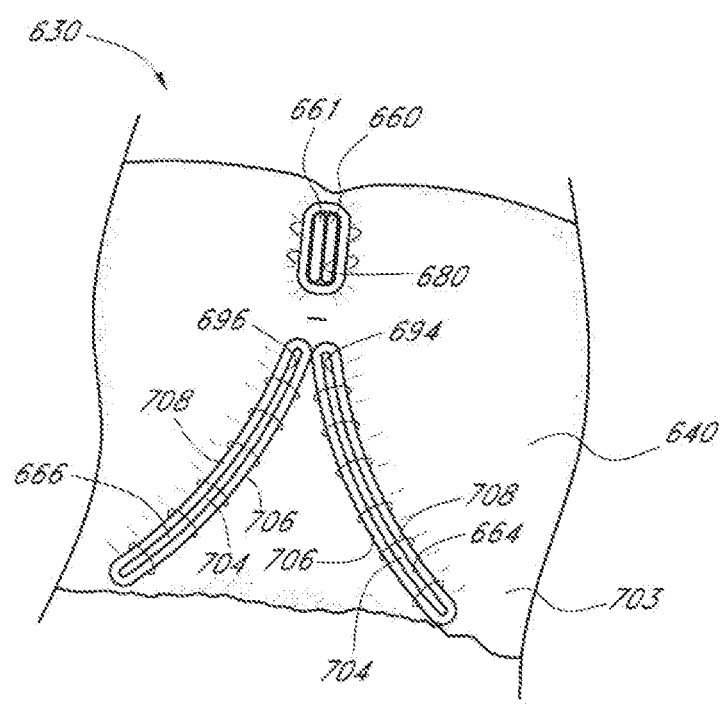
FIG. 19 depicts a perspective view of a heart valve body constructed from the pattern of FIG. 18.

With reference next to FIGS. 18 and 19, yet another embodiment of a valve body 630 is illustrated. FIG. 18 shows a flat pattern 632 for cutting the valve body 630 out of flat source tissue. As shown, the pattern 632 comprises a skirt portion 640 and a leaflet portion 650. The leaflet portion 640 comprises three leaflets 654 each having a downstream edge 662 and opposing first and second side edges 664, 666. Each leaflet 654 has opposing first and second commissural tab portions 660, 661. An offset 674 is provided between each leaflet side edge 664, 666 and the adjacent commissural tab 660, 661.

In the skirt portion 640, three commissural slits 680 are cut so as to generally align with the commissural tabs 660, 661. First and second leaflet edge slits 694, 696 are also cut in the skirt portion 640 so as to generally align with the curvature of the corresponding first and second leaflet side edges 664, 666. In the illustrated embodiment, a portion 700 of each commissural tab 660, 661 extends in the downstream direction beyond at least a portion of the leaflet downstream edge 662.

With continued reference to FIGS. 18 and 19, to construct the valve body 630 from flat tissue cut according to this pattern 632, the cut tissue is folded and the first and second leaflet edges 664, 666 are pushed through corresponding first and second leaflet slits 694, 696, respectively. Edges of the skirt portion 640 at and adjacent the leaflet slits 694, 696 preferably are deformed so that the inner surface of the skirt 640 at and adjacent the slits 694, 696 engages inner and outer surfaces of the leaflet 654 so that a leaflet cut end 704 and opposing slit cut ends 706, 708 face radially outwardly. The leaflet cut end 704 and slit cut ends 706, 708 are then sutured together. As such, the sutures connecting the leaflet edges 664, 666 to the skirt 640 are maintained generally on the outside 703 of the skirt portion 640, and portions of the leaflets 654 within the valve body 630 generally do not engage the sutures during use. Similarly, and in the manner as discussed in other embodiments, the first and second commissural tab portions 660, 661 of adjacent leaflets 654 are arranged to engage one another face-to-face, extended through the slit 680, and sewn to each other and the skirt 640 at the slit edge.

In still other embodiments, the leaflet side edges 664, 666 can be extended through corresponding slits 694, 696, folded to engage with the outer surface 703 of the skirt portion 640, and then sutured into place.

In the illustrated embodiment, the downstream portion 700 of the commissural tab portions 660, 661 contributes to surface area for sewing the commissural tab portions in place and provides material to hold onto during the manufacturing process. In some embodiments, the entire commissural tab 660, 661 is sewn to the skirt 640. In other embodiments, a portion of the tabs are sewn in place, and an unused remainder of each tab is removed and discarded.

Figure 20:
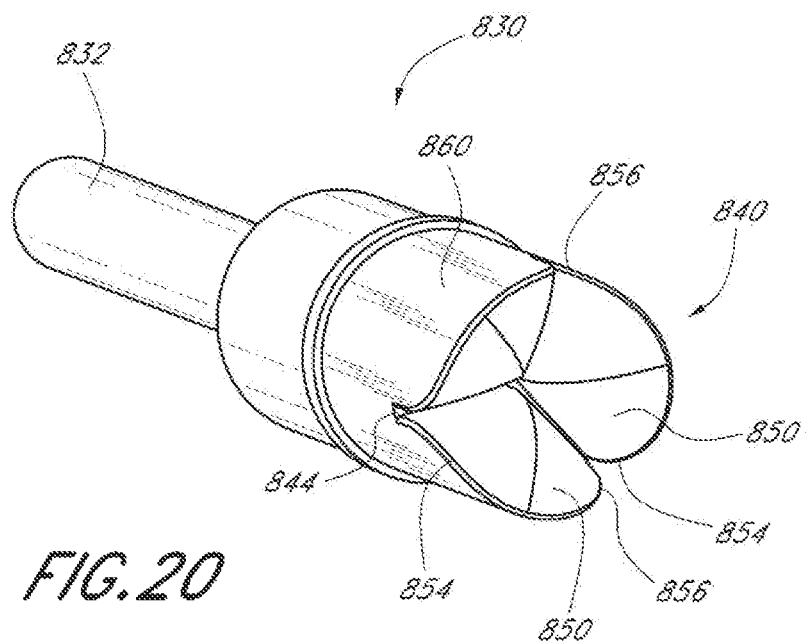
FIG. 20 is a perspective view of an embodiment of a tool for constructing a tissue valve body.

With reference next to FIG. 20, a tool 830 for helping to construct the valve body 630 of FIGS. 18 and 19 is illustrated. The tool 830 has a proximal handle portion 832 and a form 840, or mold, at its distal end. Preferably, the form 840 is shaped to be the negative of a desired shape of the downstream portion of the valve body 630 when the leaflets 654 are coapted in a closed position. The illustrated form 840 comprises a stop surface 844 and a plurality of leaflet engagement surfaces 850, each of which have first and second side edges 854, 856.

Figure 21:
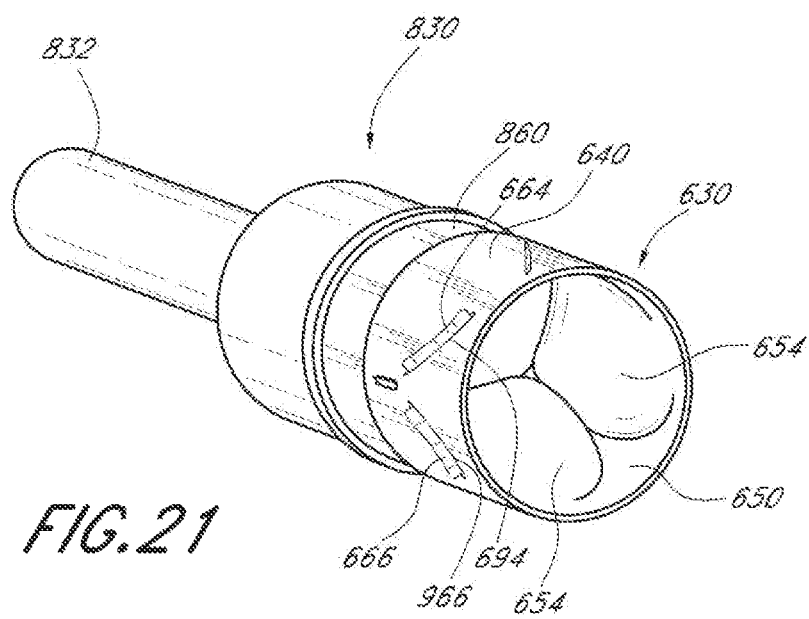
FIG. 21 shows the tool of FIG. 20 being used to construct a tissue valve body as in FIG. 18-19.
Figure 22:
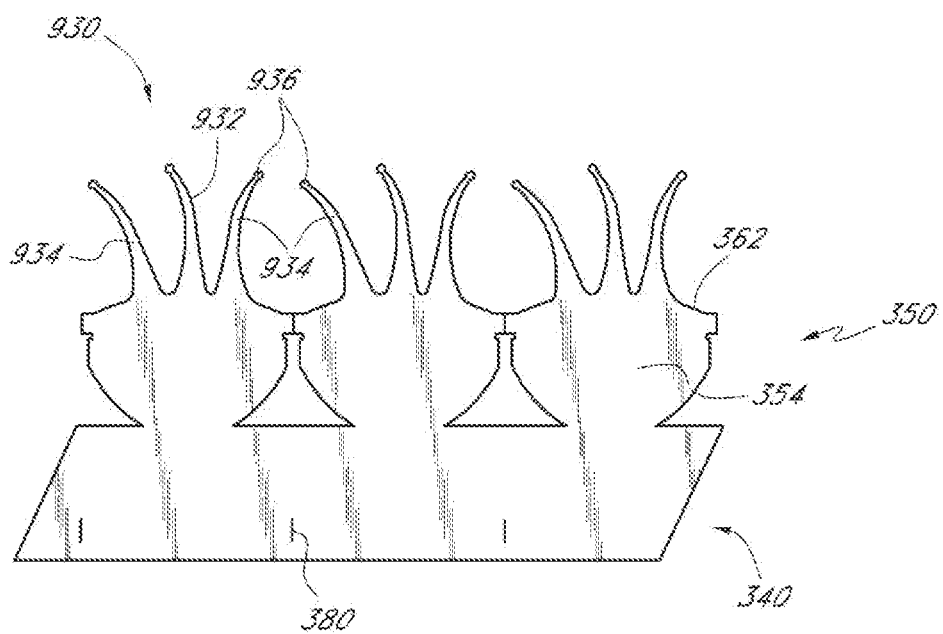
FIG. 22 shows a flat pattern for cutting a flat source tissue to form another embodiment of a valve body.

With additional reference to FIG. 21, the tool 830 is shown during construction of a valve body 630. In a preferred embodiment, the valve body 630 is cut according to the pattern 632 discussed above, and is then formed into a tube and connected at the commissural tabs 660, 661. Preferably, the commissural tabs 660, 661 are initially only tacked in place, and thus serve as a guide for placement of the partially assembled valve body 630 on the form 840. The downstream end of the partially assembled valve body 630, is then placed upon the form 840 so that the skirt 640 engages a circumferential outer surface 860 of the form, and the leaflets 654 engage corresponding leaflet engagement surfaces 850 and the first and second side edges 664, 666 of the leaflets 654 are generally aligned with the first and second side edges 854, 856 of the leaflet engagement surfaces 850. Preferably, downstream edges 662 of the leaflets 654 are at or adjacent the stop surface 844 of the form 850.

In a preferred embodiment, the operator correctly positions the valve body 630 on the form 840 and pulls side edges 664, 666 of the leaflets 654 through the corresponding leaflet slits 694, 696 of the skirt portion 640, all of which are preferably aligned with the leaflet engagement surface side edges 854, 856. In this manner, the partially-assembled valve body 630 becomes engaged with the form 840, taking on the form's shape so that the leaflets are configured in the preferred coapted position. As such, the valve body 630 can be constructed in a position that is exactly as desired for optimum valve performance. Once the valve body 630 has been properly positioned on the form 840 with the leaflet edges 664, 666 pulled through corresponding leaflet slits 694, 696, the leaflet edges 664, 666 are sewn or otherwise attached to the valve body 630 along the slits 694, 696 in any acceptable manner, including methods as discussed above. Additionally, in embodiments in which the commissural tabs were initially only tacked in place, they are then fully secured in place.

Use of the valve assembly tool 830 as discussed above enables consistent and ideal-shaped construction of a valve body in a relatively quick manner. In one embodiment, a method of creating a homologous tissue valve body is provided in which a clinician harvests a patient's own tissue, such as a patient's own pericardium, flattens the homologous source tissue, cuts it according to a desired heart valve pattern, and then assembles the valve body using the valve body assembly tool 830. Preferably, the valve can be created and then implanted by a clinician in the operating room during a single procedure.

Figure 23:
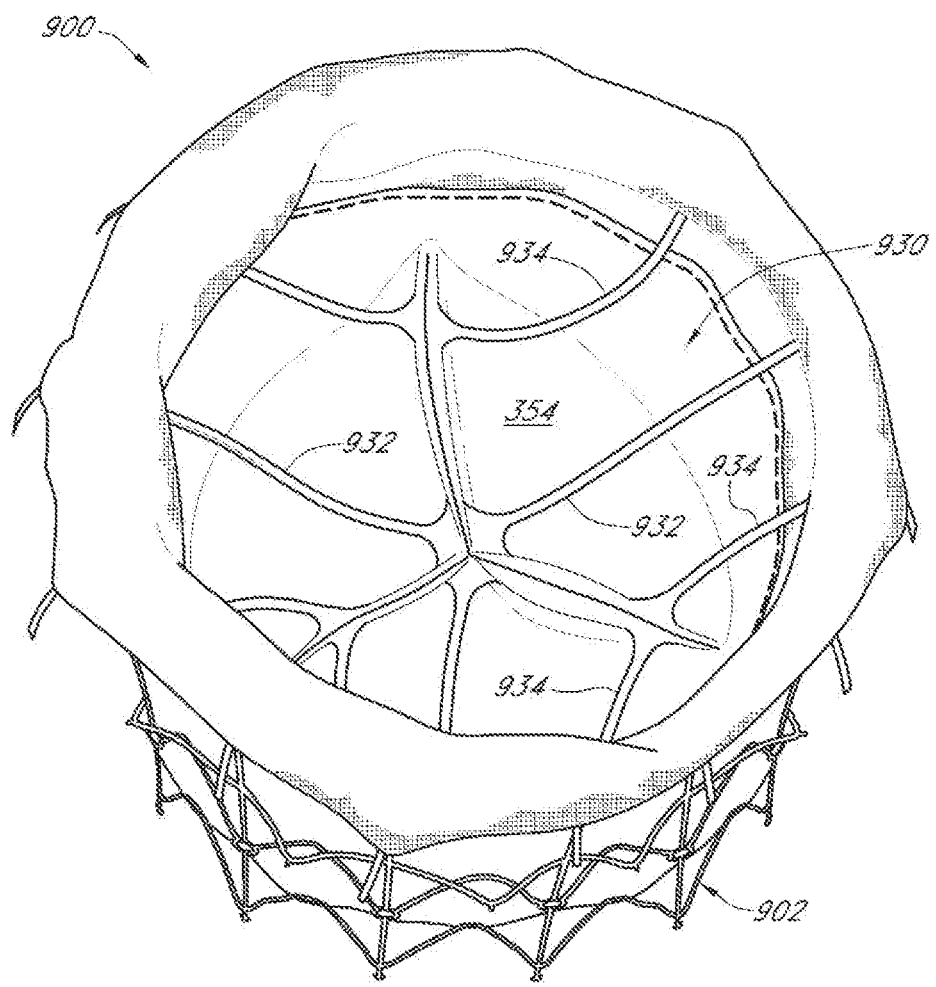
FIG. 23 is a perspective view of an embodiment of a heart valve having a valve body constructed from the pattern of FIG. 22 mounted on a stent.

With reference next to FIG. 23, another embodiment of a valve body 930 can be formed generally using much of the same pattern and manner of construction as discussed above in connection with FIGS. 7-9, with the exception that a plurality of chordae tendineae 932, 934 extend from the downstream edge 362 of each leaflet 354. In the illustrated embodiment, a central and two side chordae 932, 934 are provided. Preferably the central chordae 932 is longer than the side chordae 934. In other embodiments, more or fewer chordae may be provided. In the illustrated embodiment, the chordae 932, 934 are cut as part of the pattern, and thus are contiguous with the associated leaflet 354. Preferably a mount tab 936 is at the tip of each chord 932, 934. The mount tab 936 preferably includes an area of increased diameter that will provide space to accommodate mounting media 938 such as sutures, clips or the like.

FIG. 23 is a schematic representation of a replacement valve 900 employing the valve body 930 attached to a stent 902. Preferably the chordae 932, 934 are attached to the stent 902 downstream of the valve body which, in FIG. 23, is depicted in a closed state. As with natural chordae, preferably the chordae 932, 934 are long enough to allow the leaflets 354 to coapt fully with little or no interference, but also provide distribution of blood pressure forces during pumping of the ventricle. More simply, the chordae communicate blood pressure forces on the leaflets to the frame 902.

With additional reference to FIG. 24, a portion of the stent 902 that can be used to support the valve body 930 and chordae 932, 934 is provided. The illustrated stent is similar to the stent 500 described above. Preferably, a plurality of distal eyelets 940 is formed at or adjacent a distal end 539 of the stent. In the illustrated embodiment, the distal eyelets 940 each have a transversely elongate hole 942 with a generally flat contact surface 944. An attachment eyelet 950 is disposed on the longitudinal struts 530, preferably on the ring 522c that includes the apical anchors 550.

With specific reference to FIG. 25, a schematic representation is shown depicting a portion of the valve body 930, stent 902 and chordae 932, all in section. As shown, preferably a downstream end of the valve body is attached via sutures to the second eyelets 546 similar to embodiments discussed above. The valve body leaflets 354 are shown schematically, in phantom lines, and in a coapted state. In the illustrated embodiment, the chordae 932 extends from the leaflet and through the downstream eyelet 940. In some embodiments, the chordae can be sewn to the downstream eyelet 940. However, in the illustrated embodiment, the chordae extends through the eyelet, engages the contact surface 944, reverses course, and extends to the attachment eyelet 950. Preferably, the mount tab 936 of the chordae 932 is attached to the attachment eyelet 950 with, for example, a suture 938. In this manner, as forces from blood pressure push against the coapted leaflets of the closed valve, the chordae distribute such forces to the downstream end of the foreshortening portion of the stent and also to the upstream end of the foreshortening portion of the stent, not only distributing forces from the leaflets, but also encouraging the stent anchors 550, 570 into even more firm and secure grasping of the native valve annulus. Of course, it is to be understood that other specific areas of attachment of the chordae can be employed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. In fact, the embodiments specifically disclosed herein have been used as a vehicle to describe certain inventive features that could be employed in multiple embodiments. Thus, it is contemplated that various combinations or subcombinations of the specific features and aspects of the embodiments may be made and still fall within the scope of the invention. For example, the valve body of FIGS. 7-9 has been described in an embodiment in which adjacent commissural tabs are cut (see FIG. 9A) and in another embodiment in which commissural connections between leaflets are not cut (see FIG. 9B). However, the discussion connected with the valve body embodiment in FIG. 10 does not specifically describe an embodiment in which the commissural connections between leaflets are not cut. Since Applicant contemplates combining and/or substituting features of the discussed embodiments, it should be understood that Applicant also contemplates a variation of the FIG. 10 valve body which employs uncut commissural connections. This example applies to all of the features described herein in connection with specific embodiments. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A prosthetic heart valve comprising:
a radially expandable annular frame having an inflow end portion defining an inflow end of the frame that is configured to receive antegrade blood flow into the prosthetic heart valve when implanted within a patient's body in a radially expanded configuration, and the annular frame also having an outflow end portion defining an outflow end of the frame opposite the inflow end of the frame;
a valve body disposed inside the frame and comprising three leaflets configured to regulate the flow of blood through the frame in one direction; and
an annular inner skirt secured to an inner surface of the frame, wherein the inner skirt has an upstream edge oriented toward the inflow end of the frame, a downstream edge oriented toward the outflow end of the frame, first and second lateral edges extending from the upstream edge to the downstream edge, wherein the first lateral edge and the second lateral edge are secured together;
wherein the first lateral edge and the second lateral edge are diagonal relative to the downstream edge.

2. The prosthetic heart valve of claim 1, wherein the inner skirt is made of pericardium.

3. The prosthetic heart valve of claim 1, wherein each leaflet comprises first and second, curved leaflet side edges that are sewn to the inner skirt.

4. The prosthetic heart valve of claim 3, wherein voids are defined between adjacent side edges of adjacent leaflets and the inner skirt covers the voids.

5. The prosthetic heart valve of claim 1, wherein the frame is made of nitinol.

6. The prosthetic heart valve of claim 1, wherein the frame comprises a plurality of circumferentially extending rows of struts arranged in a zigzag pattern, including an inflow row of struts defining a plurality of inflow apices that project beyond the upstream edge of inner skirt.

7. The prosthetic heart valve of claim 1, wherein the prosthetic heart valve is adapted to replace a native aortic valve.

8. The prosthetic heart valve of claim 1, wherein the frame has an outer diameter at the inflow end of the frame and an outer diameter at the outflow end of the frame that is greater than the outer diameter at the inflow end of the frame.

9. The prosthetic heart valve of claim 1, wherein each leaflet comprises opposing commissure tab portions, wherein the commissure tab portions of the leaflets are arranged to form three commissures that are fixed relative to the frame, and the leaflets can move between open and closed states relative to the commissures.

10. The prosthetic heart valve of claim 1, the first and second lateral edges are joined together with suture material.

11. A prosthetic heart valve comprising:
a radially expandable annular frame having an inflow end portion defining an inflow end of the frame that is configured to receive antegrade blood flow into the prosthetic heart valve when implanted within a patient's body in a radially expanded configuration, and the annular frame also having an outflow end portion defining an outflow end of the frame opposite the inflow end of the frame;
three pericardium leaflets disposed inside the frame and configured to regulate the flow of blood through the frame in one direction; and
a pericardium inner skirt secured to an inner surface of the frame, wherein the inner skirt has an upstream edge oriented toward the inflow end of the frame, a downstream edge oriented toward the outflow end of the frame, first and second lateral edges extending from the upstream edge to the downstream edge, wherein the first lateral edge and the second lateral edge are secured together,
wherein the first lateral edge and the second lateral edge diagonal relative to the downstream edge;
wherein the leaflets are sewn to the inner skirt along U-shaped seams.

12. The prosthetic heart valve of claim 11, wherein each leaflet comprises first and second, curved leaflet side edges that are sewn to the inner skirt along the U-shaped seams.

13. The prosthetic heart valve of claim 12, wherein voids are defined between adjacent side edges of adjacent leaflets and the inner skirt covers the voids.

14. The prosthetic heart valve of claim 11, wherein the frame comprises a plurality of circumferentially extending rows of struts arranged in a zigzag pattern, including an inflow row of struts defining a plurality of inflow apices that project beyond the upstream edge of inner skirt.

15. The prosthetic heart valve of claim 11, wherein the inner skirt is sewn onto the frame.

16. The prosthetic heart valve of claim 11, wherein each leaflet comprises opposing commissure tab portions, wherein the commissure tab portions of the leaflets are arranged to form three commissures that are fixed relative to the frame, and the leaflets can move between open and closed states relative to the commissures.

17. The prosthetic heart valve of claim 11, wherein the first and second lateral edges are joined together with suture material.

18. The prosthetic heart valve of claim 11, wherein the frame has an outer diameter at the inflow end of the frame and an outer diameter at the outflow end of the frame that is greater than the outer diameter at the inflow end of the frame.

19. A prosthetic heart valve comprising:
a radially expandable annular frame having an inflow end portion defining an inflow end of the frame that is configured to receive antegrade blood flow into the prosthetic heart valve when implanted within a patient's body in a radially expanded configuration, and the annular frame also having an outflow end portion defining an outflow end of the frame opposite the inflow end of the frame, wherein the frame comprises a plurality of circumferentially extending rows of struts arranged in a zigzag pattern, including an inflow row of struts defining a plurality of inflow apices;
three pericardium leaflets disposed inside the frame and configured to regulate the flow of blood through the frame in one direction, wherein each leaflet comprises opposing commissure tab portions, wherein the commissure tab portions of the leaflets are arranged to form three commissures that are fixed relative to the frame, and outflow edges of the leaflets can move between open and closed states relative to the commissures; and
a pericardium inner skirt secured to an inner surface of the frame, wherein the inner skirt has an upstream edge oriented toward the inflow end of the frame, a downstream edge oriented toward the outflow end of the frame, first and second lateral edges extending from the upstream edge to the downstream edge, wherein the first lateral edge and the second lateral edge are secured together;
wherein the first lateral edge and the second lateral edge diagonal relative to the downstream edge;

wherein the inflow apices project beyond the upstream edge of inner skirt;

wherein each leaflet comprises first and second, curved leaflet side edges that are sewn to the inner skirt and wherein voids are defined between adjacent side edges of adjacent leaflets and the inner skirt extends between and covers the voids.

20. The prosthetic heart valve of claim 18, the first and second lateral edges are joined together with suture material.

* * * * *